United States Patent
Yokoyama et al.

(10) Patent No.: US 12,089,488 B2
(45) Date of Patent: Sep. 10, 2024

(54) ORGANIC ELECTROLUMINESCENT DEVICE

(71) Applicant: Hodogaya Chemical Co., Ltd., Tokyo (JP)

(72) Inventors: Norimasa Yokoyama, Tokyo (JP); Shuichi Hayashi, Tokyo (JP); Shigeru Kusano, Tsukuba (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 313 days.

(21) Appl. No.: 16/211,756

(22) Filed: Dec. 6, 2018

(65) Prior Publication Data

US 2019/0115542 A1 Apr. 18, 2019

Related U.S. Application Data

(63) Continuation of application No. 14/343,530, filed as application No. PCT/JP2012/005665 on Sep. 6, 2012, now abandoned.

(30) Foreign Application Priority Data

Sep. 12, 2011 (JP) ................................ 2011-198221

(51) Int. Cl.
H10K 85/60 (2023.01)
C07C 211/54 (2006.01)
(Continued)

(52) U.S. Cl.
CPC .......... H10K 85/626 (2023.02); C07D 209/88 (2013.01); C07D 213/38 (2013.01);
(Continued)

(58) Field of Classification Search
CPC ............... H01L 51/0058; H01L 51/005; H01L 51/0052; H01L 51/0059; H01L 51/006;
(Continued)

(56) References Cited

U.S. PATENT DOCUMENTS

| 5,792,557 A | 8/1998 | Nakaya et al. |
| 2001/0000005 A1* | 3/2001 | Forrest .................. C09K 11/06 |
| | | 257/E33.056 |

(Continued)

FOREIGN PATENT DOCUMENTS

| CN | 101133504 A | 2/2008 |
| CN | 101484412 A | 7/2009 |

(Continued)

OTHER PUBLICATIONS

Fujino et al., machine translation of JP-2000169448-A (2001) pp. 1-19. (Year: 2001).*

(Continued)

*Primary Examiner* — Dylan C Kershner
(74) *Attorney, Agent, or Firm* — Locke Lord LLP; James E. Armstrong, IV; Nicholas J. DiCeglie, Jr.

(57) ABSTRACT

An organic electroluminescent device having a capping layer composed of material having a high refractive index, excelling in thin film stability and durability and having no absorption in the respective wavelength ranges of blue, green, and red is provided to improve device characteristics of the organic electroluminescent device, particularly to greatly improve light extraction efficiency. The organic electroluminescent device has at least an anode electrode, a hole transport layer, a light emitting layer, an electron transport layer, a cathode electrode, and the capping layer in this order, wherein the capping layer contains an arylamine compound (X) having a structure in which two triphenylamine structures are joined within a molecule via a single bond or a divalent group that does not contain a heteroatom.

17 Claims, 1 Drawing Sheet

(51) Int. Cl.
  *C07C 211/58* (2006.01)
  *C07D 209/88* (2006.01)
  *C07D 213/38* (2006.01)
  *C07D 333/76* (2006.01)
  *C09B 57/00* (2006.01)
  *H10K 50/15* (2023.01)
  *H10K 50/844* (2023.01)
  *H10K 50/858* (2023.01)

(52) U.S. Cl.
  CPC .......... *C07D 333/76* (2013.01); *C09B 57/008* (2013.01); *H10K 85/60* (2023.02); *H10K 85/615* (2023.02); *H10K 85/631* (2023.02); *H10K 85/633* (2023.02); *H10K 85/636* (2023.02); *H10K 85/654* (2023.02); *H10K 85/6572* (2023.02); *H10K 85/6576* (2023.02); *C07C 211/54* (2013.01); *C07C 211/58* (2013.01); *H10K 50/15* (2023.02); *H10K 50/844* (2023.02); *H10K 50/858* (2023.02)

(58) Field of Classification Search
  CPC ............. H01L 51/0061; H01L 51/0067; H01L 51/0072; H01L 51/0074; C07D 209/88; C07D 213/38; C07D 333/76; C07C 211/54; C07C 211/55; C07C 211/57; C07C 211/58; C07C 211/60; C07C 211/06; H10K 50/858
  USPC ............. 428/690, 691, 917; 427/58, 66; 313/500–512; 257/40, 88–104, 257/E51.001–51.052; 252/301.16–301.35
  See application file for complete search history.

(56) References Cited

U.S. PATENT DOCUMENTS

| | | |
|---|---|---|
| 2002/0182439 A1 | 12/2002 | Tao et al. |
| 2006/0021647 A1 | 2/2006 | Gui et al. |
| 2006/0113907 A1 | 6/2006 | Im et al. |
| 2007/0296331 A1* | 12/2007 | Yabunouchi .......... C07C 211/58 313/504 |
| 2008/0023724 A1 | 1/2008 | Takeda et al. |
| 2009/0115315 A1 | 5/2009 | Takaya et al. |
| 2009/0179559 A1 | 7/2009 | Yoon et al. |
| 2011/0112275 A1 | 5/2011 | Parham et al. |
| 2012/0138918 A1* | 6/2012 | Naraoka ................ C09K 11/06 257/40 |
| 2012/0161107 A1 | 6/2012 | Yokoyama et al. |
| 2012/0292609 A1 | 11/2012 | Yokoyama et al. |

FOREIGN PATENT DOCUMENTS

| | | | |
|---|---|---|---|
| CN | 102057514 A | | 5/2011 |
| EP | 2145936 A2 | | 1/2010 |
| JP | H07188130 A | | 7/1995 |
| JP | 08-048656 A | | 2/1996 |
| JP | 2000169448 A | * | 6/2000 |
| JP | 3398548 B2 | | 4/2003 |
| JP | 2006-049890 A | | 2/2006 |
| JP | 2006-156390 A | | 6/2006 |
| JP | 2006-302879 A | | 11/2006 |
| JP | 2009-135511 A | | 6/2009 |
| JP | 2009-170885 A | | 7/2009 |
| JP | WO 2011043083 A1 | * | 4/2011 .............. C09K 11/06 |
| WO | 2008/001551 A1 | | 1/2008 |
| WO | 2009/104148 A1 | | 8/2009 |
| WO | 2009/151039 A1 | | 12/2009 |
| WO | 2011/043083 A1 | | 4/2011 |
| WO | 2011/093056 A1 | | 8/2011 |

OTHER PUBLICATIONS

Office Action mailed Feb. 19, 2019, issued for the Japanese patent application No. 2018-019901.
International Search Report dated Oct. 23, 2012, issued for PCT/JP2012/005665.
Supplementary European Search Report dated Jul. 6, 2015, issued for the European patent application No. 12832163.5.
Office Action issued in corresponding Japanese Patent Application No. JP 2013-533483, dated Mar. 7, 2017.
Japanese Translation of Office Action issued in corresponding Chinese Patent Application No. CN 201610105370.0, dated Feb. 3, 2017.
Anzai et al., machine translation of JP-07188130-A, pp. 1-17, (1995).
Machine translation of JP 3398548 B2, Date of Japanese Lamguage Document: Apr. 2003, pp. 1-11.
Aonuma et al., "Material design of hole transport materials capable of thick-film formation in organic light emitting diodes", 2007, Applied Physics Letters, vol. 90, article 183503, pp. 1-3.
Shirota et al., "Thermally stable organic light-emitting diodes using new families of hole-transporting amorphous molecular materials", 2000, Synthetic Metals, vol. 111-112, pp. 387-391.

* cited by examiner

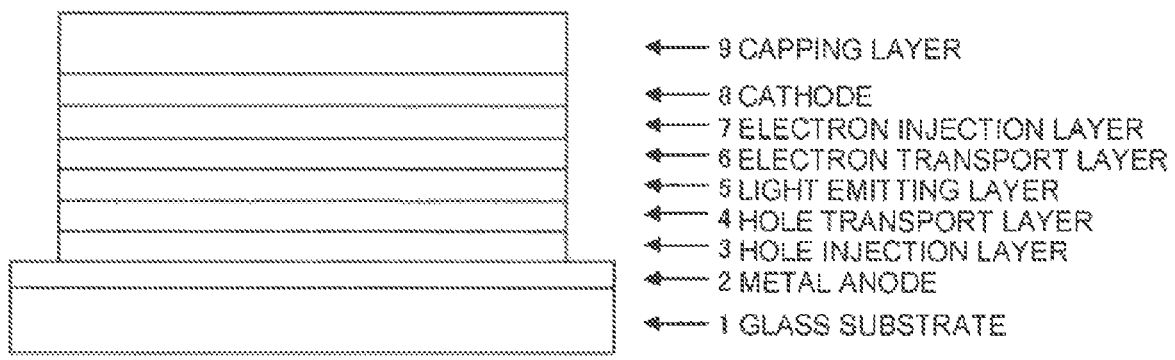

ORGANIC ELECTROLUMINESCENT DEVICE

CROSS REFERENCE TO RELATED APPLICATIONS

This Application is a Continuation of U.S. patent application Ser. No. 14/343,530, filed Mar. 7, 2014, which application is a § 371 U.S. National Phase of International PCT Patent Application No. PCT/JP2012/005665, filed Sep. 6, 2012, which application claims priority to Japanese Patent Application No. 2011-198221 filed Sep. 12, 2011. The entire contents of these applications are incorporated herein by reference in their entirety.

TECHNICAL FIELD

The present invention relates to an organic electroluminescent device (hereinafter referred to as an organic EL device) which is a preferred self-luminous device for various display devices. Specifically, this invention relates to an organic EL device using a specific arylamine derivative, particularly an organic EL device greatly improved in light extraction efficiency.

BACKGROUND ART

The organic EL device is a self-luminous device and has been actively studied for their brighter, superior visibility and the ability to display clearer images in comparison with liquid crystal devices.

In 1987, C. W. Tang and colleagues at Eastman Kodak developed a laminated structure device using materials assigned with different roles, realizing practical applications of an organic EL device with organic materials. These researchers laminated an electron-transporting phosphor and a hole-transporting organic substance, and injected both charges into a phosphor layer to cause emission in order to obtain a high luminance of 1,000 cd/m$^2$ or more at a voltage of 10 V or less (refer to Patent Documents 1 and 2, for example).

To date, various improvements have been made for practical applications of the organic EL device. Various roles of the laminated structure are further subdivided to provide an electroluminescence device that includes an anode, a hole injection layer, a hole transport layer, a light emitting layer, an electron transport layer, an electron injection layer, and a cathode successively formed on a substrate, wherein high efficiency and durability are achieved by a light emitting device of bottom emission structure that emits light from the bottom (refer to Non-Patent Document 1, for example).

Light emitting devices of top emission structure that emit light from the top using metal with a high work function as an anode have been used in recent years. Unlike the light emitting device of bottom emission structure restricted in the area of a light emitting part by a pixel circuit, the light emitting device of top emission structure has an advantage of having a wide light emitting part. In the light emitting device of top emission structure, a semitransparent electrode of LiF/Al/Ag (refer to Non-patent document 2, for example), Ca/Mg (refer to Non-patent document 3, for example), LiF/MgAg, or the like is used as a cathode.

In such a light emitting device, when light emitted in a light emitting layer is incident on the other film, if the light is incident at a certain angle or more, the light is totally reflected on an interface between the light emitting layer and the other film. Consequently, only a part of the emitted light has been used. In recent years, a light emitting device provided with a "capping layer" with a high refractive index, on the outside of a semitransparent electrode with a low refractive index has been proposed to improve light extraction efficiency (refer to Non-patent documents 2 and 3, for example).

The capping layer in the light emitting device of top emission structure has an effect that the light emitting device using Ir(ppy)$_3$ as a light emitting material has a current efficiency of 38 cd/A in the case of having no capping layer, while a light emitting device using ZnSe with a film thickness of 60 nm as the capping layer has a current efficiency of 64 cd/A, that is, the efficiency improvement of about 1.7 times is recognized. It is also indicated that the maximum point of transmittance of the semitransparent electrode and the capping layer does not necessarily coincide with the maximum point of efficiency, and it is indicated that the maximum point of light extraction efficiency is determined by an interference effect (refer to Non-patent document 3, for example).

The use of a metal mask of high definition is proposed for the formation of the capping layer. However, in such a metal mask, there has been a problem of worsening alignment accuracy due to distortion caused by heat. That is, ZnSe has a high melting point of 1,100° C. or higher (refer to Non-patent document 3, for example), and vapor deposition in an accurate position is impeded in the mask of high definition. Many inorganic substances have high vapor deposition temperatures and are unsuitable for the use of the mask of high definition, and there is a possibility of damaging the light emitting device itself. Further, since the light emitting device is damaged in film formation by a sputtering method, the capping layer containing an inorganic substance as a constitutive material cannot be used.

In the case of using tris(8-hydroxyquinoline)aluminum (hereinafter, referred to as "Alq$_3$") as the capping layer for adjusting a refractive index (refer to Non-patent document 2, for example), although Alq$_3$ is known as an organic EL material generally used as a green light emitting material or an electron transport material, it has weak absorption in the vicinity of 450 nm used for a blue light emitting device. In consequence, there has been a problem of causing a decrease in color purity and a decrease in light extraction efficiency in the case of the blue light emitting device.

A material having a high refractive index and excelling in thin film stability and durability is demanded as a material for the capping layer to improve device characteristics of the organic EL device, particularly to greatly improve light extraction efficiency.

CITATION LIST

Patent Documents

Patent Document 1: JP-A-8-48656
Patent Document 2: Japanese Patent No. 3194657
Patent Document 3: JP-A-7-126615
Patent Document 4: JP-A-8-48656
Patent Document 5: JP-2005-108804

Non-Patent Documents

Non-Patent Document 1: The Japan Society of Applied Physics, 9th Lecture Preprints, pp. 55 to 61 (2001)
Non-Patent Document 2: Appl. Phys. Lett., 78, 544 (2001)

Non-Patent Document 3: Appl. Phys. Lett., 82, 466 (2003)

SUMMARY OF THE INVENTION

Problems to be Solved by the Invention

An object of the present invention is to provide an organic EL device having a capping layer composed of a material having a high refractive index, excelling in thin film stability and durability and having no absorption in the respective wavelength regions of blue, green and red colors to improve device characteristics of the organic EL device, particularly to greatly improve light extraction efficiency.

Physical properties of the material of the capping layer suitable for the present invention include (1) a high refractive index, (2) vapor deposition ability without causing thermal decomposition, (3) a stable thin film state, and (4) a high glass transition temperature. Physical properties of the device suitable for the present invention include (1) high light extraction efficiency, (2) no decrease in color purity, (3) light transmission without changes with the lapse of time, and (4) a long life.

Means for Solving the Problems

In order to achieve the above objects, the present inventors noted that an arylamine-based material excels in thin film stability and durability, selected a specific arylamine compound with a high refractive index, produced an organic EL device using the specific arylamine compound as a material for composing a capping layer, and completed the present invention after thorough evaluations of the device characteristics.

Specifically, the following organic EL device is provided according to the present invention.

1) An organic EL device including at least an anode electrode, a hole transport layer, a light emitting layer, an electron transport layer, a cathode electrode and a capping layer in this order, wherein the capping layer includes an arylamine compound (X) having a structure in which two triphenylamine structures are joined within a molecule via a single bond or a divalent group that does not contain a heteroatom.

2) The organic EL device of 1), wherein the arylamine compound (X) having a structure in which two triphenylamine structures are joined within a molecule via a single bond or a divalent group that does not contain a heteroatom is an arylamine compound (X') represented by the following general formula (1).

[Chemical Formula 1]

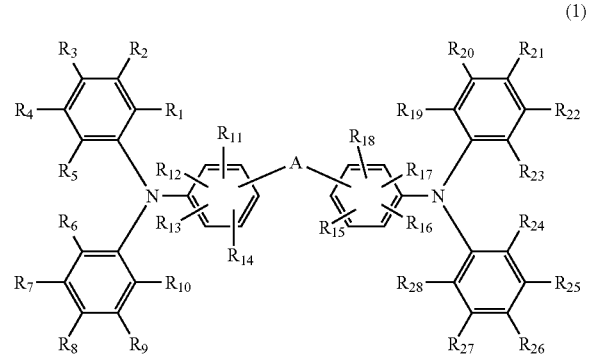

(1)

In the formula, $R_1$ to $R_{28}$ may be the same or different, and each represents a hydrogen atom, a deuterium atom, a fluorine atom, a chlorine atom, cyano, trifluoromethyl, nitro, linear or branched alkyl of 1 to 6 carbon atoms that may have a substituent, linear or branched alkenyl of 2 to 6 carbon atoms that may have a substituent, cycloalkyl of 5 to 10 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy. These substituents may bind to each other to form a ring when a plurality of these substituents bind to the same benzene ring, and $R_1$ to $R_{10}$ and $R_{19}$ to $R_{28}$ may form rings by binding to benzene rings to which the respective groups bind. A represents a divalent group represented by the following structural formulae (B) to (F), or a single bond, where when A is a single bond, at least one of $R_1$ to $R_{28}$ is a substituted or unsubstituted aromatic hydrocarbon group.

[Chemical Formula 2]

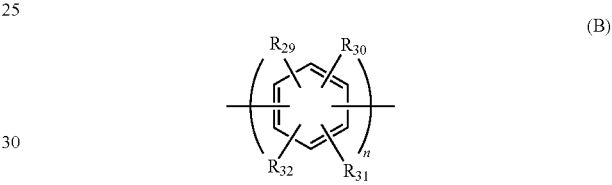

(B)

In the formula, $R_{29}$ to $R_{32}$ may be the same or different, and each represents a hydrogen atom, a deuterium atom, a fluorine atom, a chlorine atom, cyano, trifluoromethyl, linear or branched alkyl of 1 to 6 carbon atoms, linear or branched alkenyl of 2 to 6 carbon atoms, a substituted or unsubstituted aromatic hydrocarbon group, a substituted or unsubstituted aromatic heterocyclic group, or a substituted or unsubstituted condensed polycyclic aromatic group. These substituents may bind to each other to form a ring when a plurality of these substituents bind to the same benzene ring, and n is an integer of 1 to 3. When a plurality of each of $R_{29}$ to $R_{32}$ are present (when n is 2 or 3), $R_{29}$ to $R_{32}$ may be the same or different.

[Chemical Formula 3]

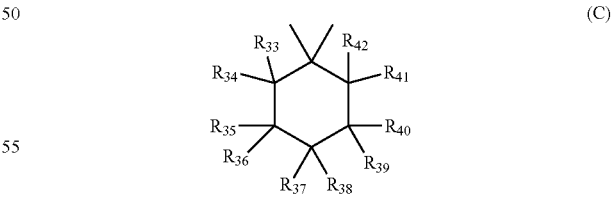

(C)

In the formula, $R_{33}$ to $R_{42}$ may be the same or different, and each represents a hydrogen atom, a deuterium atom, a fluorine atom, a chlorine atom, cyano, trifluoromethyl, linear or branched alkyl of 1 to 6 carbon atoms, linear or branched alkenyl of 2 to 6 carbon atoms, a substituted or unsubstituted aromatic hydrocarbon group, a substituted or unsubstituted aromatic heterocyclic group, or a substituted or unsubstituted condensed polycyclic aromatic group. These substituents may bind to each other to form a ring.

[Chemical Formula 4]

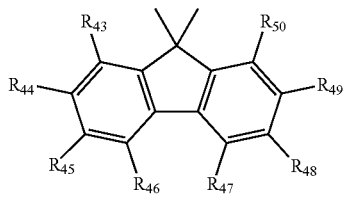

(D)

In the formula, $R_{43}$ to $R_{50}$ may be the same or different, and each represents a hydrogen atom, a deuterium atom, a fluorine atom, a chlorine atom, cyano, trifluoromethyl, linear or branched alkyl of 1 to 6 carbon atoms, linear or branched alkenyl of 2 to 6 carbon atoms, a substituted or unsubstituted aromatic hydrocarbon group, a substituted or unsubstituted aromatic heterocyclic group, or a substituted or unsubstituted condensed polycyclic aromatic group. These substituents may bind to each other to form a ring.

[Chemical Formula 5]

(E)

[Chemical Formula 6]

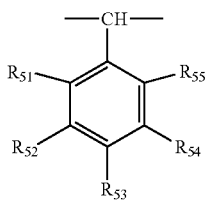

(F)

In the formula, $R_{51}$ to $R_{55}$ may be the same or different, and each represents a hydrogen atom, a deuterium atom, a fluorine atom, a chlorine atom, cyano, trifluoromethyl, linear or branched alkyl of 1 to 6 carbon atoms, linear or branched alkenyl of 2 to 6 carbon atoms, a substituted or unsubstituted aromatic hydrocarbon group, a substituted or unsubstituted aromatic heterocyclic group, or a substituted or unsubstituted condensed polycyclic aromatic group. These substituents may bind to each other to form a ring.

3) The organic EL device of 2), wherein the A is a divalent group represented by the structural formula (B).

4) The organic EL device of 3), wherein the A is a divalent group represented by the structural formula (B), and n is 1.

5) The organic EL device of 2), wherein the A is a single bond.

6) The organic EL device of 2), wherein the A is a divalent group represented by the structural formula (D).

7) The organic EL device of 1) to 6), wherein the thickness of the capping layer is within a range of 30 nm to 120 nm.

8) The organic EL device of any one of 1) to 7), wherein the refractive index of the capping layer is 1.75 or more when the wavelength of light that transmits the capping layer is within a range of 530 nm to 750 nm.

Specific examples of the "linear or branched alkyl of 1 to 6 carbon atoms", "cycloalkyl of 5 to 10 carbon atoms", or "linear or branched alkenyl of 2 to 6 carbon atoms" in the "linear or branched alkyl of 1 to 6 carbon atoms that may have a substituent", "cycloalkyl of 5 to 10 carbon atoms that may have a substituent", or "linear or branched alkenyl of 2 to 6 carbon atoms that may have a substituent" represented by $R_1$ to $R_{28}$ in the general formula (1) include methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl. These substituents may bind to each other to form a ring. $R_1$ to $R_{10}$ and $R_{19}$ to $R_{28}$ may form rings by binding to benzene rings to which the respective groups bind, via a single bond, substituted or unsubstituted methylene, an oxygen atom, a sulfur atom, or N—Ar. "N" in "N—Ar" represents a nitrogen atom, and "Ar" represents a "substituted or unsubstituted aromatic hydrocarbon group", a "substituted or unsubstituted aromatic heterocyclic group", or a "substituted or unsubstituted condensed polycyclic aromatic group", and can be the same groups exemplified as the aromatic hydrocarbon group, the aromatic heterocyclic group or the condensed polycyclic aromatic group in $R_1$ to $R_{28}$ below. Substituents that these groups may have can be the same substituents exemplified for the same groups in $R_1$ to $R_{28}$ below.

Specific examples of the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by $R_1$ to $R_{28}$ in the general formula (1) include a deuterium atom; trifluoromethyl; cyano; nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkyloxys of 1 to 6 carbon atoms such as methyloxy, ethyloxy, and propyloxy; alkenyls such as allyl; aralkyls such as benzyl, naphthylmethyl, and phenethyl; aryloxys such as phenyloxy and tolyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; aromatic heterocyclic groups such as pyridyl, furanyl, pyranyl, thienyl, pyrrolyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyls such as styryl and naphthylvinyl; acyls such as acetyl and benzoyl; dialkylamino groups such as dimethylamino and diethylamino; disubstituted amino groups such as diphenylamino and dinaphthylamino, substituted with aromatic hydrocarbon groups or condensed polycyclic aromatic groups; diaralkylamino groups such as dibenzylamino and diphenethylamino; disubstituted amino groups such as dipyridylamino and dithienylamino, substituted with aromatic heterocyclic groups; dialkenylamino groups such as diallylamino; and disubstituted amino groups substituted with a substituent selected from alkyl, an aromatic hydrocarbon group, a condensed polycyclic aromatic group, aralkyl, an aromatic heterocyclic group, and alkenyl. These substituents may be further substituted with other substituents.

Specific examples of the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of 5 to 10 carbon atoms that may have a substituent" represented by $R_1$ to $R_{28}$ in the general formula (1) include methyloxy, ethyloxy, n-propyloxy, isopropyloxy, n-butyloxy, tert-butyloxy, n-pentyloxy, n-hexyloxy, cyclopentyloxy, cyclohexyloxy, cycloheptyloxy, cyclooctyloxy, 1-adamantyloxy, and 2-adamantyloxy. These substituents may bind to each other to form a ring. $R_1$ to $R_{10}$ and $R_{19}$ to $R_{28}$ may form rings by binding to benzene rings to which the respective groups bind, via a single bond, substituted or unsubstituted methylene, an oxygen atom, a sulfur atom, or N—Ar. "N" in "N—Ar" represents a nitrogen atom, and "Ar" represents a "substituted or unsubstituted aromatic hydrocarbon group", a "substituted or unsubstituted aromatic heterocyclic group", or a "substituted or unsubstituted condensed polycyclic aromatic group", and can be the same groups exemplified as the aromatic hydrocarbon group, the aromatic heterocyclic group or the condensed polycyclic aromatic group in $R_1$ to $R_{28}$ below. Substituents that these groups may have can be the same substituents exemplified for the same groups in $R_1$ to $R_{28}$ below.

Specific examples of the "substituent" in the "linear or branched alkyloxy of 1 to 6 carbon atoms that has a substituent" or the "cycloalkyloxy of 5 to 10 carbon atoms that has a substituent" represented by $R_1$ to $R_{28}$ in the general formula (1) include a deuterium atom; trifluoromethyl; cyano; nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, n-hexyl; linear or branched alkyloxys of 1 to 6 carbon atoms such as methyloxy, ethyloxy, and propyloxy; alkenyls such as allyl; aralkyls such as benzyl, naphthylmethyl, and phenethyl; aryloxys such as phenyloxy and tolyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; aromatic heterocyclic groups such as pyridyl, furanyl, pyranyl, thienyl, pyrrolyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyls such as styryl and naphthylvinyl; acyls such as acetyl and benzoyl; dialkylamino groups such as dimethylamino and diethylamino; disubstituted amino groups such as diphenylamino and dinaphthylamino, substituted with aromatic hydrocarbon groups or condensed polycyclic aromatic groups; diaralkylamino groups such as dibenzylamino and diphenethylamino; disubstituted amino groups such as dipyridylamino and dithienylamino, substituted with aromatic heterocyclic groups; dialkenylamino groups such as diallylamino; and disubstituted amino groups substituted with a substituent selected from alkyl, an aromatic hydrocarbon group, a condensed polycyclic aromatic group, aralkyl, an aromatic heterocyclic group, and alkenyl. These substituents may be further substituted with other substituents.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_1$ to $R_{28}$ in the general formula (1) include phenyl, biphenylyl, terphenylyl, naphthyl, anthryl, phenanthryl, fluorenyl, indenyl, pyrenyl, perylenyl, fluoranthenyl, triphenylenyl, pyridyl, furanyl, pyranyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl. These substituents may bind to each other to form a ring. $R_1$ to $R_{10}$ and $R_{19}$ to $R_{28}$ may form rings by binding to benzene rings to which the respective groups bind, via a single bond, substituted or unsubstituted methylene, an oxygen atom, a sulfur atom, or N—Ar. "N" in "N—Ar" represents a nitrogen atom, and "Ar" represents a "substituted or unsubstituted aromatic hydrocarbon group", a "substituted or unsubstituted aromatic heterocyclic group", or a "substituted or unsubstituted condensed polycyclic aromatic group", and can be the same groups as exemplified above. Substituents that these groups may have can be the same substituents as exemplified below.

Specific examples of the "substituent" in the "substituted aromatic hydrocarbon group", the "substituted aromatic heterocyclic group", or the "substituted condensed polycyclic aromatic group" represented by $R_1$ to $R_{28}$ in general formula (1) include a deuterium atom; cyano; trifluoromethyl; nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; cycloalkyls of 5 to 10 carbon atoms such as cyclopentyl and cyclohexyl; linear or branched alkenyls of 2 to 6 carbon atoms such as vinyl, allyl, 2-butenyl, and 1-hexenyl; linear or branched alkyloxys of 1 to 6 carbon atoms such as methyloxy, ethyloxy, and propyloxy; cycloalkyloxys of 5 to 10 carbon atoms such as cyclopentyloxy and cyclohexyloxy; aralkyls such as benzyl, naphthylmethyl, and phenethyl; aryloxys such as phenyloxy, tolyloxy, biphenylyloxy, terphenylyloxy, naphthyloxy, anthryloxy, phenanthryloxy, fluorenyloxy, indenyloxy, pyrenyloxy, and perylenyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; aromatic heterocyclic groups such as pyridyl, furanyl, pyranyl, thienyl, pyrrolyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyls such as styryl and naphthylvinyl; acyls such as acetyl and benzoyl; dialkylamino groups such as dimethylamino and diethylamino; disubstituted amino groups such as diphenylamino and dinaphthylamino, substituted with aromatic hydrocarbon groups or condensed polycyclic aromatic groups; diaralkylamino groups such as dibenzylamino and diphenethylamino; disubstituted amino groups such as dipyridylamino and dithienylamino, substituted with aromatic heterocyclic groups; dialkenylamino groups such as diallylamino; and disubstituted amino groups substituted with a substituent selected from alkyl, an aromatic hydrocarbon group, a condensed polycyclic aromatic group, aralkyl, an aromatic heterocyclic group, and alkenyl. These substituents may be further substituted with other substituents.

Specific examples of the "aryloxy" in the "substituted or unsubstituted aryloxy" represented by $R_1$ to $R_{28}$ in general formula (1) include phenyloxy, tolyloxy, biphenylyloxy, terphenylyloxy, naphthyloxy, anthryloxy, phenanthryloxy, fluorenyloxy, indenyloxy, pyrenyloxy, and perylenyloxy. These substituents may bind to each other to form a ring. $R_1$ to $R_{10}$ and $R_{19}$ to $R_{28}$ may form rings by binding to benzene rings to which the respective groups bind, via a single bond, substituted or unsubstituted methylene, an oxygen atom, a sulfur atom, or N—Ar. "N" in "N—Ar" represents a nitrogen atom, and "Ar" represents a "substituted or unsubstituted aromatic hydrocarbon group", a "substituted or unsubstituted aromatic heterocyclic group", or a "substituted or unsubstituted condensed polycyclic aromatic group", and can be the same groups exemplified as the aromatic hydrocarbon group, the aromatic heterocyclic group or the condensed polycyclic aromatic group in $R_1$ to $R_{28}$ above. Substituents that these groups may have can be the same substituents exemplified for the same groups in $R_1$ to $R_{28}$ above.

Specific examples of the "substituent" in the "substituted aryloxy" represented by $R_1$ to $R_{28}$ in general formula (1) include a deuterium atom; cyano; trifluoromethyl; nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; cycloalkyls of 5 to 10 carbon atoms such as cyclopentyl and cyclohexyl; linear or branched alkenyls of 2 to 6 carbon atoms such as vinyl, allyl, 2-butenyl, and 1-hexenyl; linear or branched alkyloxys of 1 to 6 carbon atoms such as methyloxy, ethyloxy, and propyloxy; cycloalkyloxys of 5 to 10 carbon atoms such as cyclopentyloxy and cyclohexyloxy; aralkyls such as benzyl, naphthylmethyl, and phenethyl; aryloxys such as phenyloxy, tolyloxy, biphenylyloxy, terphenylyloxy, naphthyloxy, anthryloxy, phenanthryloxy, fluorenyloxy, indenyloxy, pyrenyloxy, and perylenyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; aromatic heterocyclic groups such as pyridyl, furanyl, pyranyl, thienyl, pyrrolyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyls such as styryl and naphthylvinyl; acyls such as acetyl and benzoyl; dialkylamino groups such as dimethylamino and diethylamino; disubstituted amino groups such as diphenylamino and dinaphthylamino, substituted with aromatic hydrocarbon groups or condensed polycyclic aromatic groups; diaralkylamino groups such as dibenzylamino and diphenethylamino; disubstituted amino groups such as dipyridylamino and dithienylamino, substituted with aromatic heterocyclic groups; dialkenylamino groups such as diallylamino; and disubstituted amino groups substituted with a substituent selected from alkyl, an aromatic hydrocarbon group, a condensed polycyclic aromatic group, aralkyl, an aromatic heterocyclic group, and alkenyl. These substituents may be further substituted with other substituents.

Specific examples of the "linear or branched alkyls of 1 to 6 carbon atoms" or the "linear or branched alkenyls of 2 to 6 carbon atoms" represented by $R_{29}$ to $R_{55}$ in structural formulae (B) to (D) and (F), corresponding to A in general formula (1), include methyl, ethyl, n-propyl, isopropyl, n-butyl, isobutyl, tert-butyl, n-pentyl, isopentyl, neopentyl, n-hexyl, vinyl, allyl, isopropenyl, and 2-butenyl. These substituents may form a ring by binding to each other via a single bond, substituted or unsubstituted methylene, an oxygen atom, or a sulfur atom. In the case of forming the ring, it is preferable that the substituents bind to each other via a single bond or dimethylmethylene to form the ring.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_{29}$ to $R_{55}$ in structural formulae (B) to (D) and (F), corresponding to A in general formula (1), include phenyl, biphenylyl, terphenylyl, tetrakisphenyl, styryl, naphthyl, anthryl, acenaphthenyl, fluorenyl, phenanthryl, indenyl, pyrenyl, pyridyl, pyrimidyl, furanyl, pyrrolyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, naphthyridinyl, phenanthrolinyl, and acridinyl. These substituents may form a ring by binding to each other via a single bond, substituted or unsubstituted methylene, an oxygen atom, or a sulfur atom when a plurality of these substituents bind to the same benzene ring. In the case of forming the ring, it is preferable that the substituents bind to each other via a single bond or dimethylmethylene to form the ring.

Specific examples of the "substituent" in the "substituted aromatic hydrocarbon group", "substituted aromatic heterocyclic group", or "substituted condensed polycyclic aromatic group" represented by $R_{29}$ to $R_{55}$ in structural formulae (B) to (D) and (F), corresponding to A in general formula (1), include a deuterium atom, a fluorine atom, a chlorine atom, trifluoromethyl, linear or branched alkyl of 1 to 6 carbon atoms, phenyl, biphenylyl, terphenylyl, tetrakisphenyl, styryl, naphthyl, fluorenyl, phenanthryl, indenyl, and pyrenyl. These substituents may be further substituted. These substituents may form a ring by binding to each other via a single bond, substituted or unsubstituted methylene, an oxygen atom, or a sulfur atom. In the case of forming the ring, it is preferable that the substituents bind to each other via a single bond or dimethylmethylene to form the ring.

The arylamine compound (X) having a structure in which two triphenylamine structures are joined within a molecule via a single bond or a divalent group that does not contain a heteroatom, for use in the organic EL device of the present invention, can be used as a constitutive material of a hole injection layer, a hole transport layer, a light emitting layer, an electron blocking layer, or a capping layer of an organic EL device.

In the organic EL device of the present invention, the thickness of the capping layer is preferably in a range of 30 nm to 120 nm, further preferably in a range of 40 nm to 80 nm.

In the organic EL device of the present invention, the refractive index of the capping layer when the wavelength of light transmitted through the capping layer is within a range of 530 nm to 750 nm, is preferably 1.75 or more, further preferably 1.80 or more.

In the organic EL device of the present invention, the capping layer may be prepared by laminating two or more kinds of different constitutive materials.

Effects of the Invention

The organic EL device of the present invention can be greatly improved in light extraction efficiency because of having the capping layer that is provided outside the transparent or semitransparent electrode and that has a refractive index higher than that of the semitransparent electrode. Since a specific arylamine compound having a structure in which two triphenylamine structures are joined within a molecule via a single bond or a divalent group that does not contain a heteroatom, is used for the capping layer, a film can be formed at a temperature of 400° C. or lower to prevent the damage of a light emitting device. Further, a high-definition mask is used to optimize the extraction efficiency of light of each color, and the organic EL device can be suitably applied to a full-color display to permit the display of a clear, light image with high color purity.

In the organic EL device of the present invention, since a material for the organic EL device having a high refractive index and excelling in thin film stability and durability is used as the material for the capping layer, light extraction efficiency can be greatly improved in comparison with conventional organic EL devices. Further, the organic EL device of high efficiency with a long life can be achieved.

BRIEF DESCRIPTION OF THE DRAWINGS

The FIGURE is a diagram illustrating the configuration of the organic EL devices of Examples 3 to 10 and Comparative Example 1.

MODE FOR CARRYING OUT THE INVENTION

The arylamine compound having a structure in which two triphenylamine structures are joined within a molecule via a single bond or a divalent group that does not contain a heteroatom, represented by the general formula (1) and suitably used for the organic EL device of the present invention, may be synthesized by a known method (refer to Patent documents 3 to 5, for example).

The following presents specific examples of particularly preferred compounds among the arylamine compounds (X') each having a structure in which two triphenylamine structures are joined within a molecule via a single bond or a divalent group that does not contain a heteroatom, represented by the general formula (1) and suitably used for the organic EL device of the present invention. The present invention, however, is not restricted to these compounds.

[Chemical Formula 7]

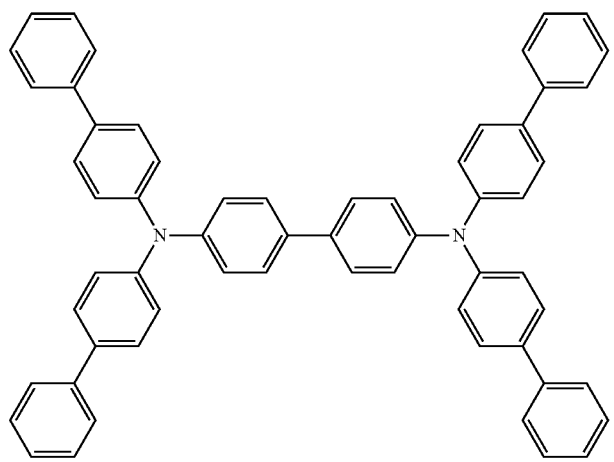

(1-1)

[Chemical Formula 8]

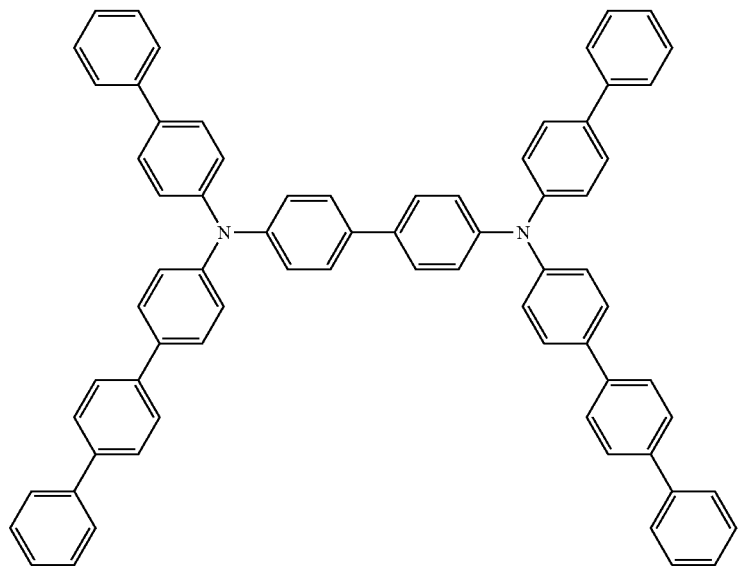

(1-2)

[Chemical Formula 9]
(1-3)
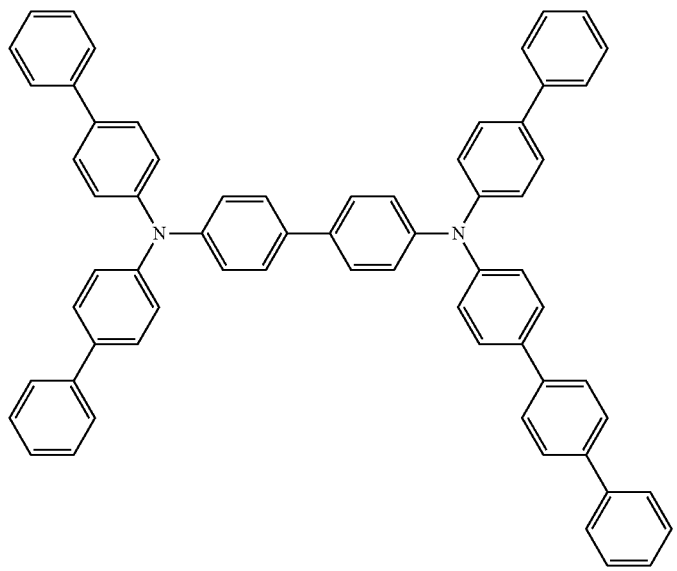
[Chemical Formula 10]
(1-4)
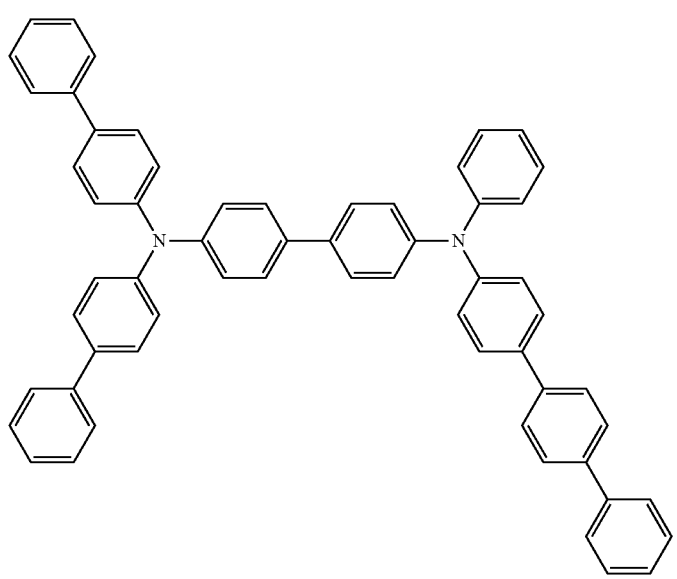

[Chemical Formula 11]
(1-5)
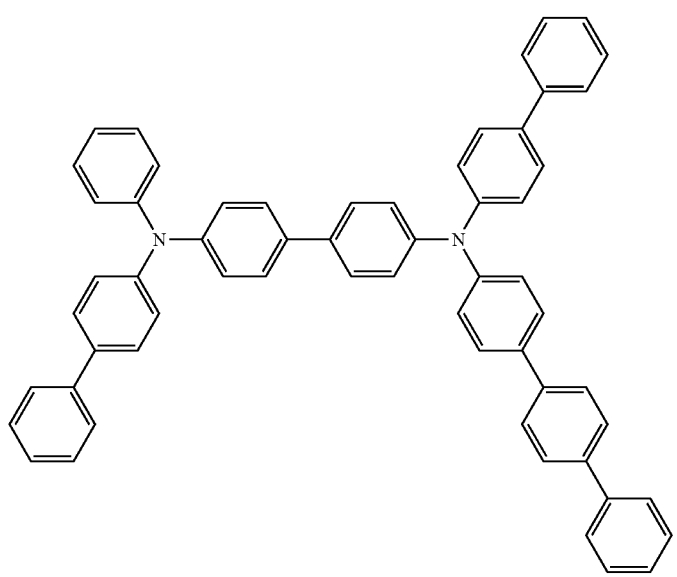
[Chemical Formula 12]
(1-6)
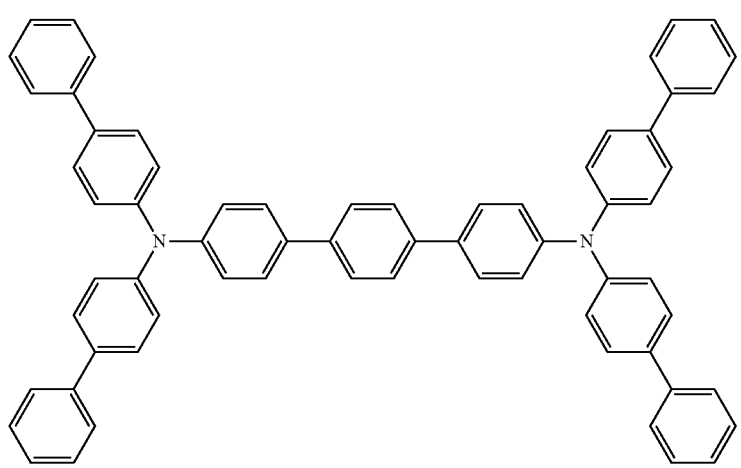
[Chemical Formula 13]
(1-7)
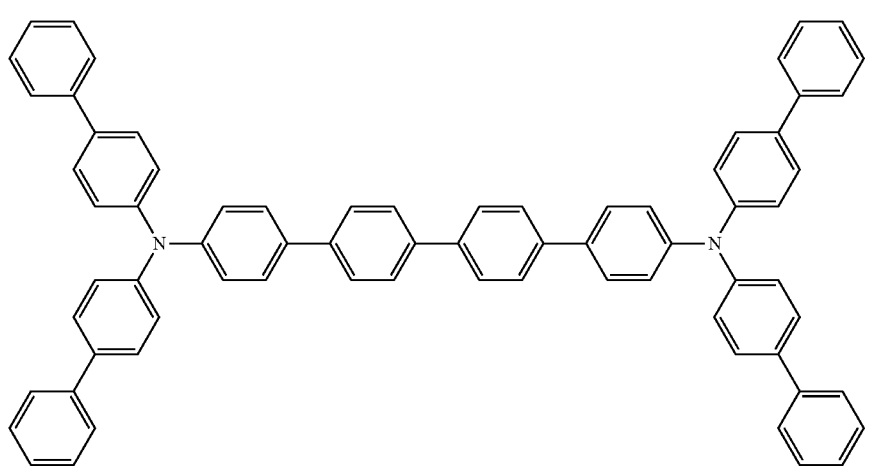

[Chemical Formula 14]
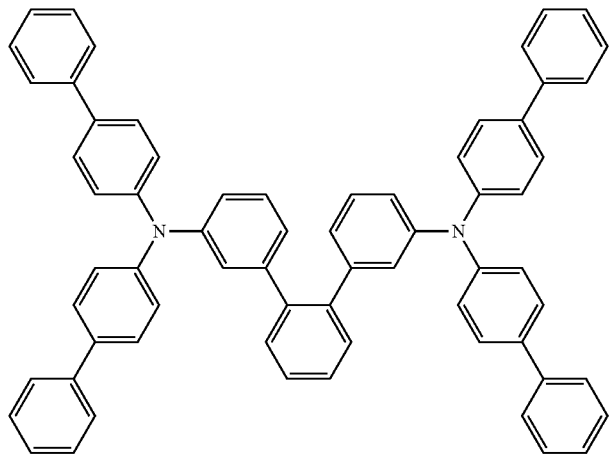
(1-8)
[Chemical Formula 15]
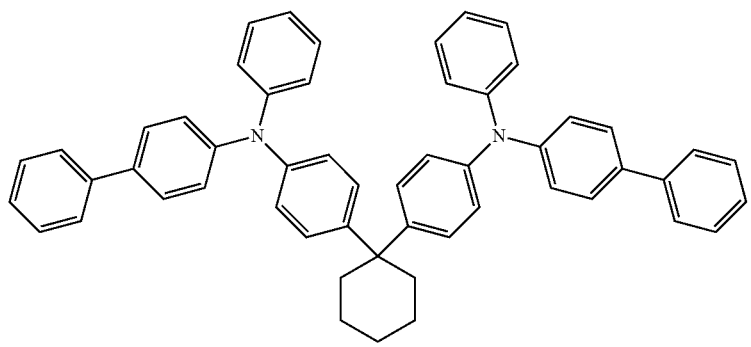
(1-9)
[Chemical Formula 16]
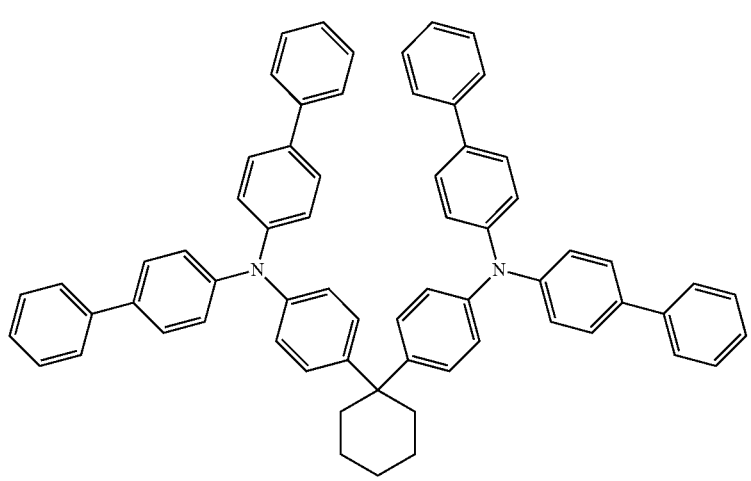
(1-10)

[Chemical Formula 17]
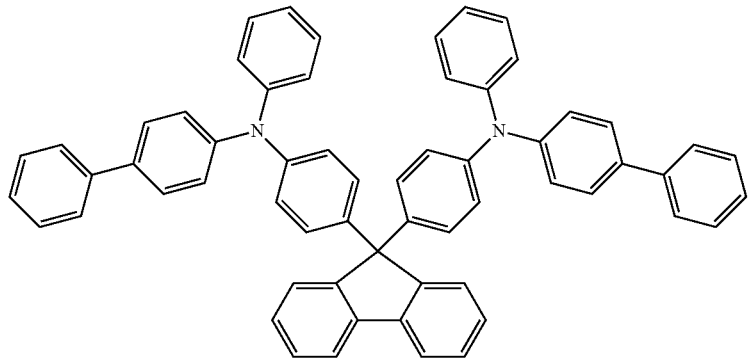
(1-11)
[Chemical Formula 18]
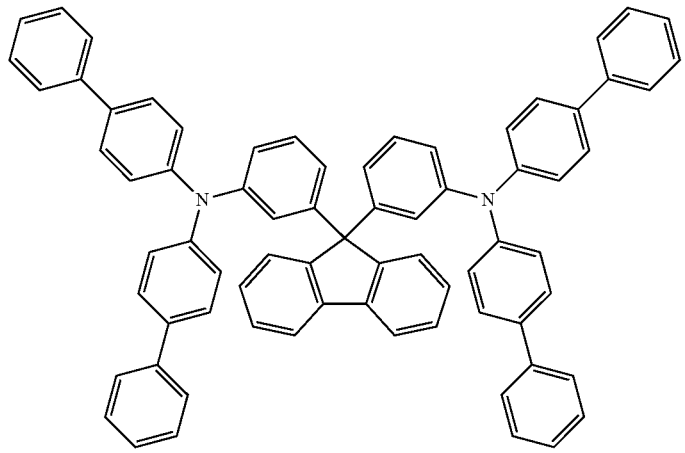
(1-12)
[Chemical Formula 19]
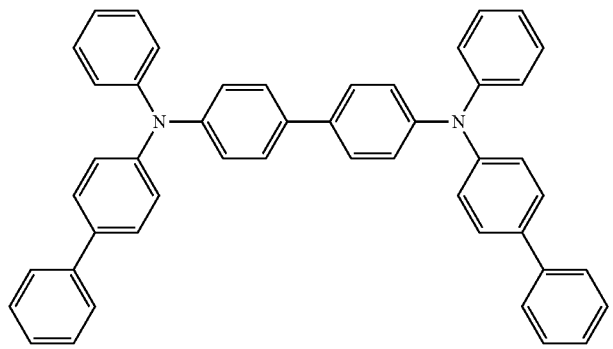
(1-13)

[Chemical Formula 20]
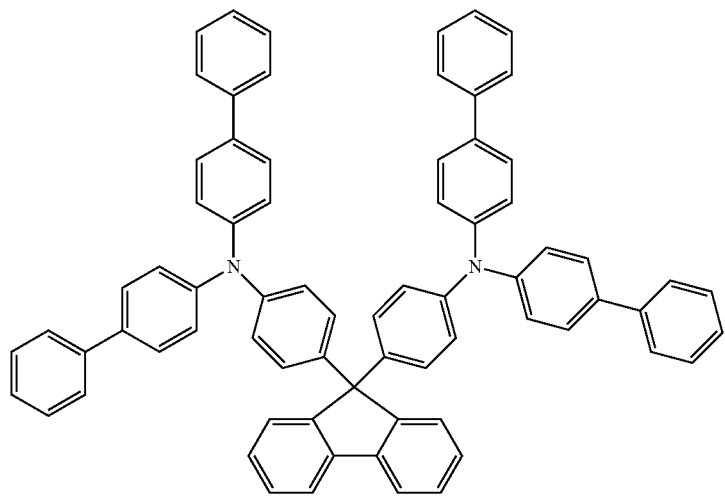
(1-14)
[Chemical Formula 21]
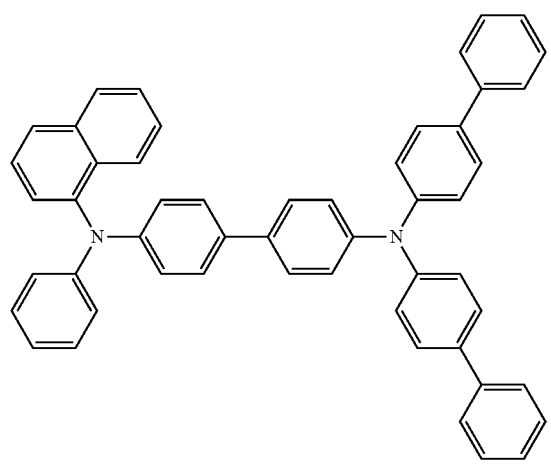
(1-15)
[Chemical Formula 22]
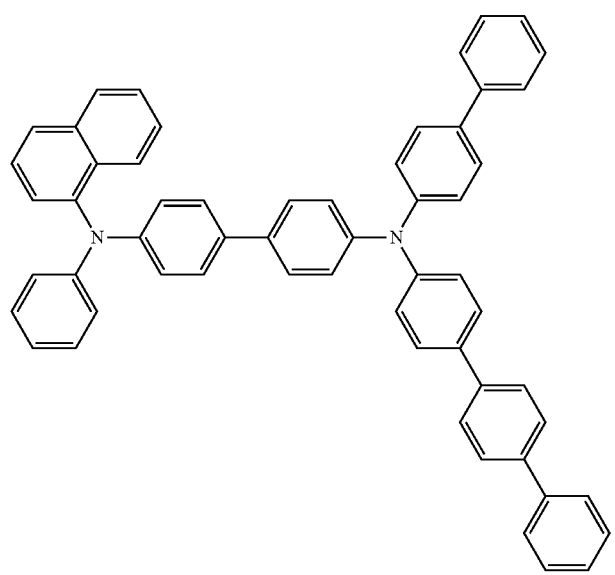
(1-16)

[Chemical Formula 23]
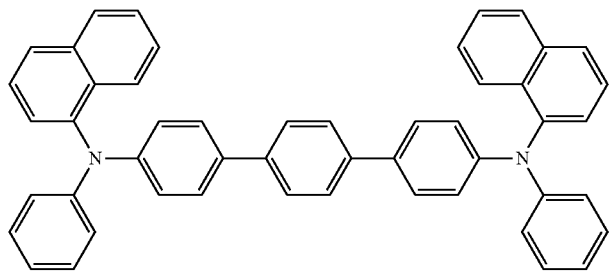
(1-17)
[Chemical Formula 24]
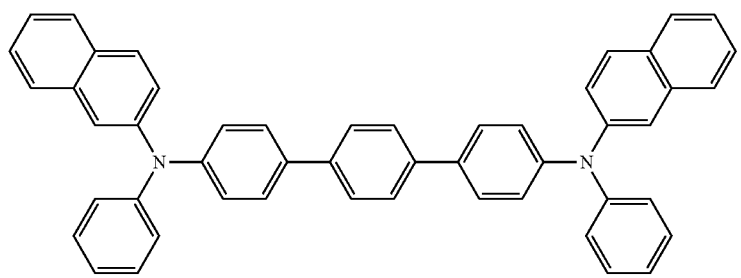
(1-18)
[Chemical Formula 25]
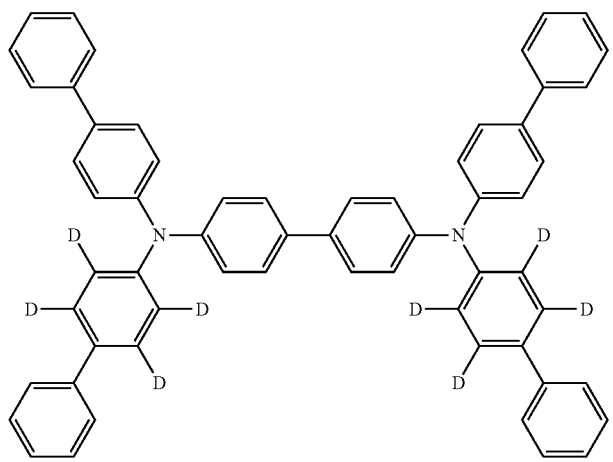
(1-19)
[Chemical Formula 26]
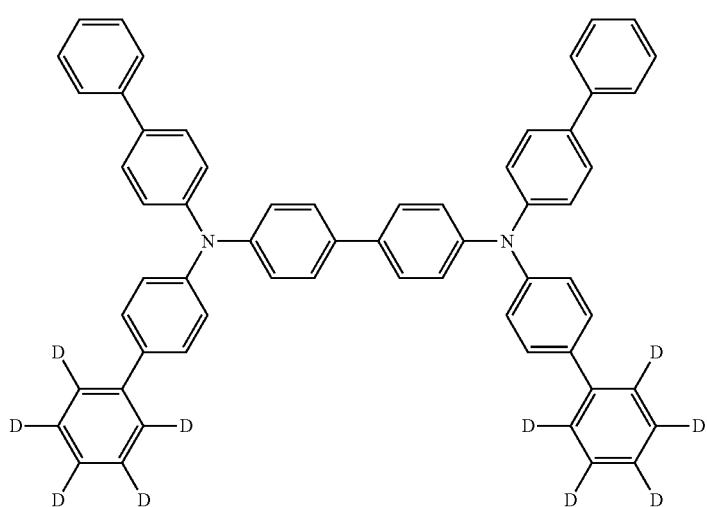
(1-20)

[Chemical Formula 27]
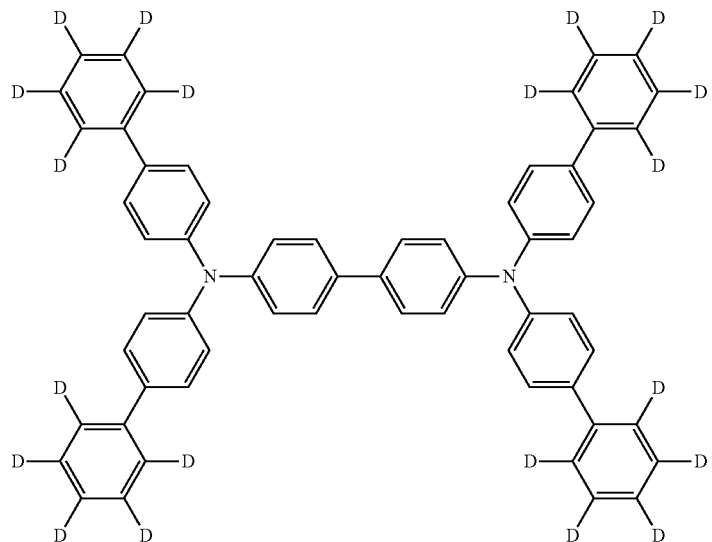
(1-21)
[Chemical Formula 28]
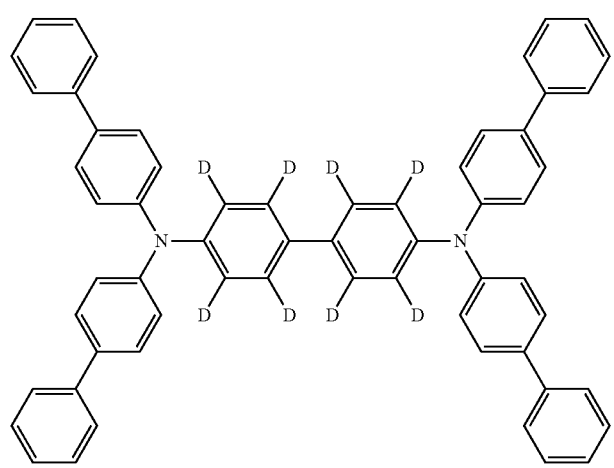
(1-22)
[Chemical Formula 29]
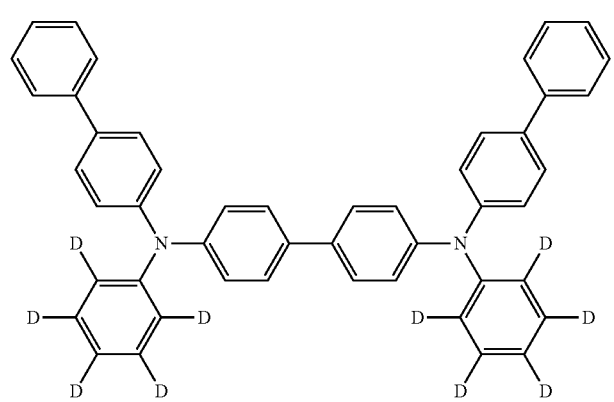
(1-23)

[Chemical Formula 30]
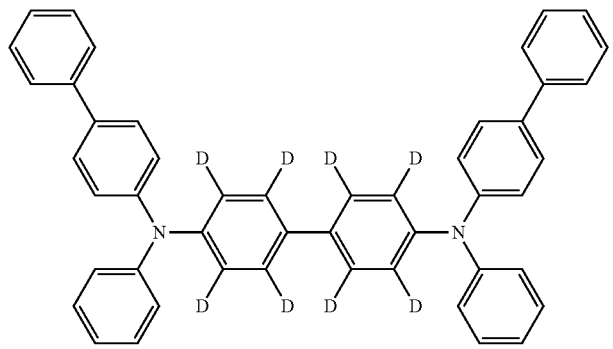
(1-24)
[Chemical Formula 31]
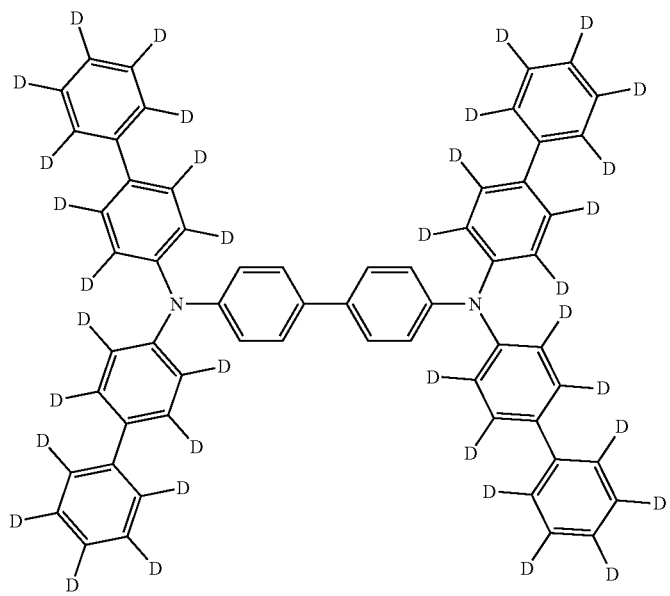
(1-25)
[Chemical Formula 32]
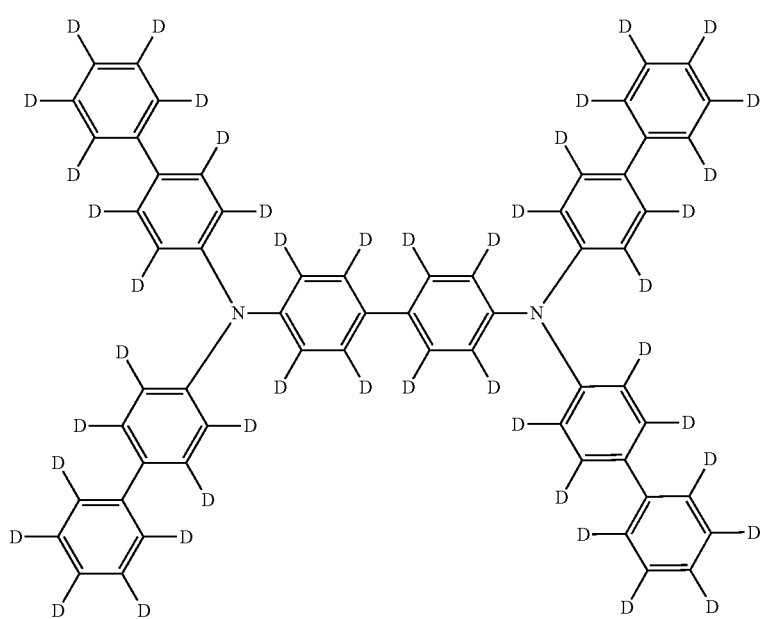
(1-26)

[Chemical Formula 33]
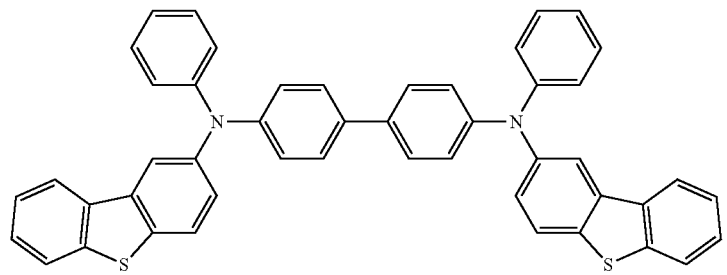
(1-27)
[Chemical Formula 34]
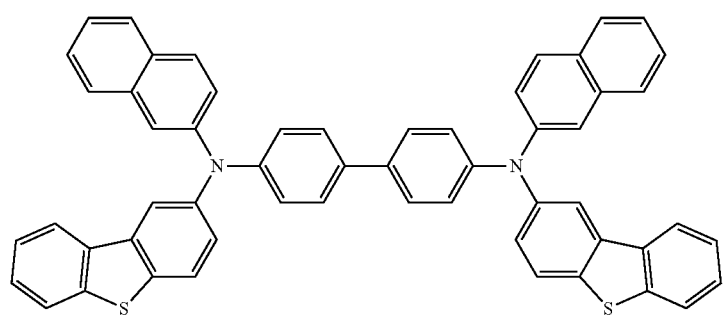
(1-28)
[Chemical Formula 35]
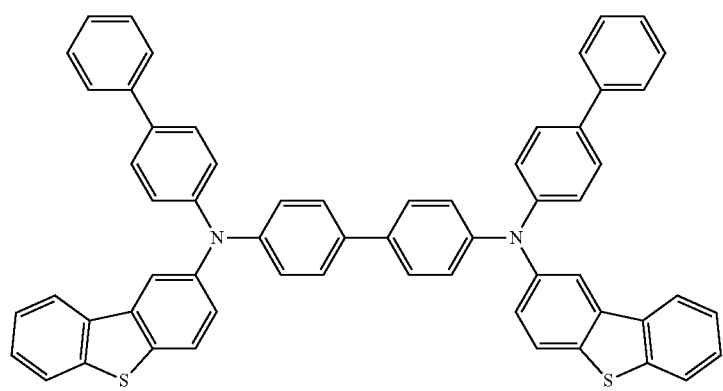
(1-29)
[Chemical Formula 36]
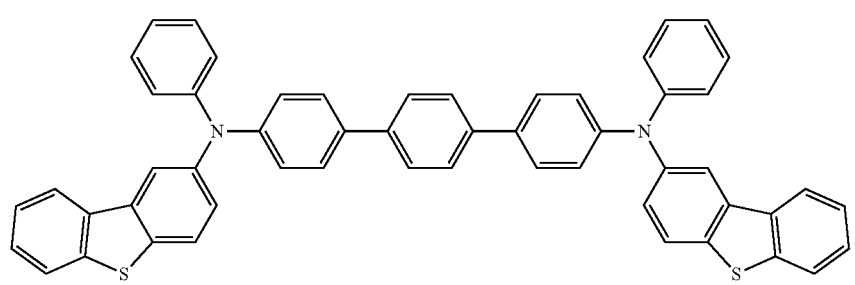
(1-30)

[Chemical Formula 37]
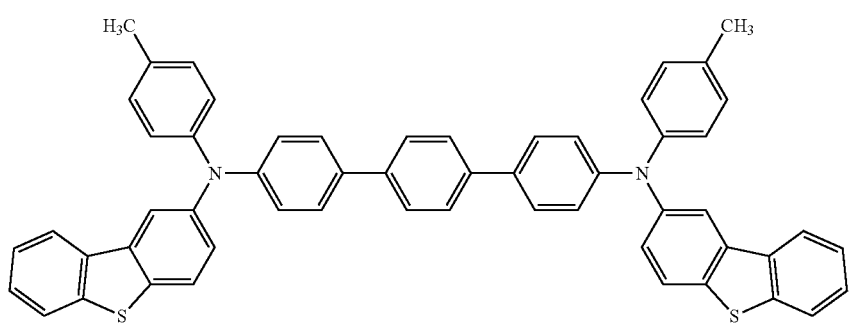
(1-31)
[Chemical Formula 38]
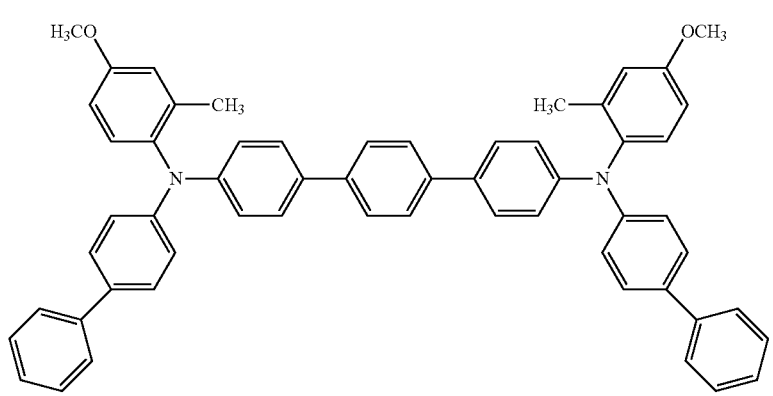
(1-32)
[Chemical Formula 39]
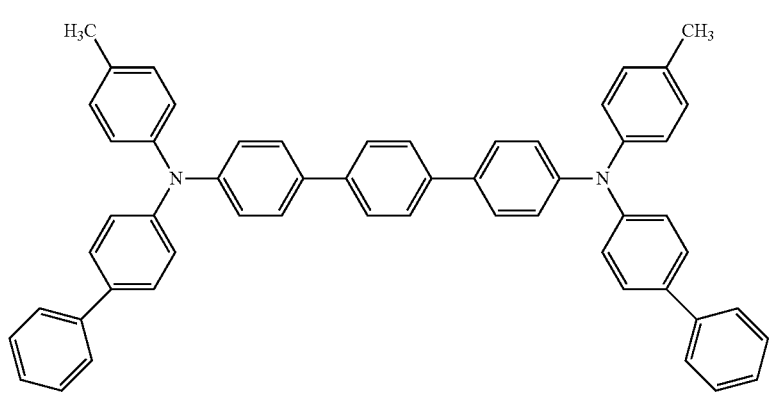
(1-33)
[Chemical Formula 40]
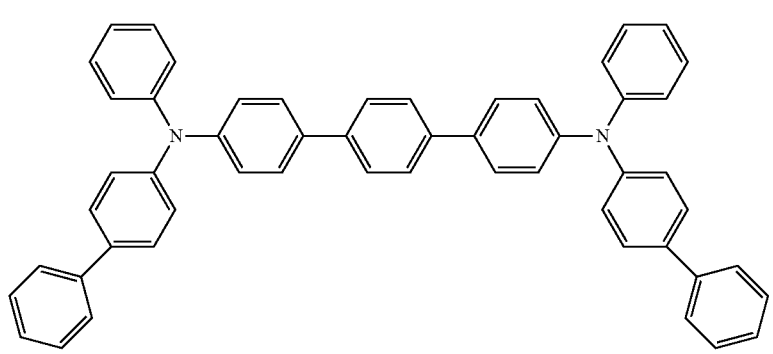
(1-34)

[Chemical Formula 41]
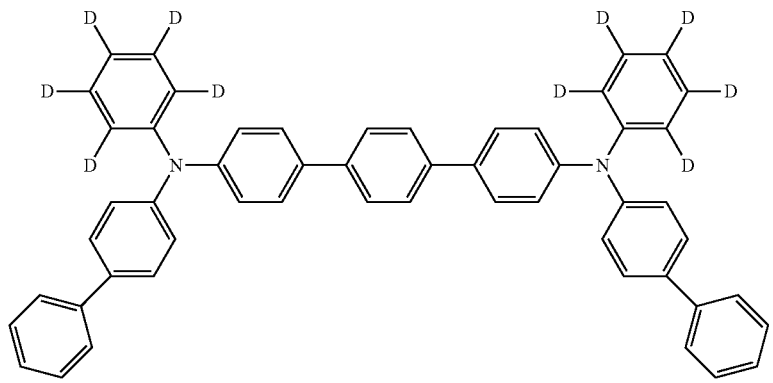
(1-35)
[Chemical Formula 42]
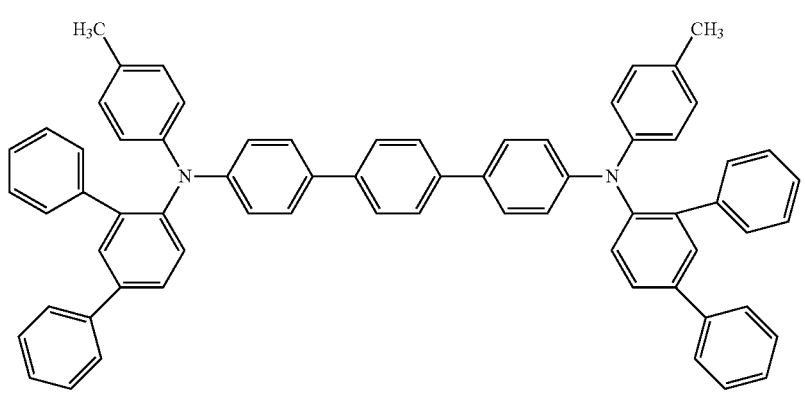
(1-36)
[Chemical Formula 43]
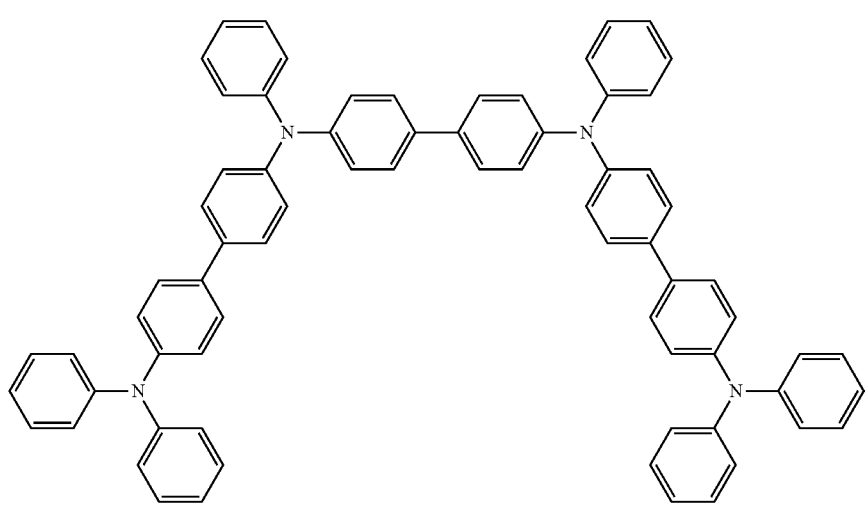
(1-37)

[Chemical Formula 44]
(1-38)
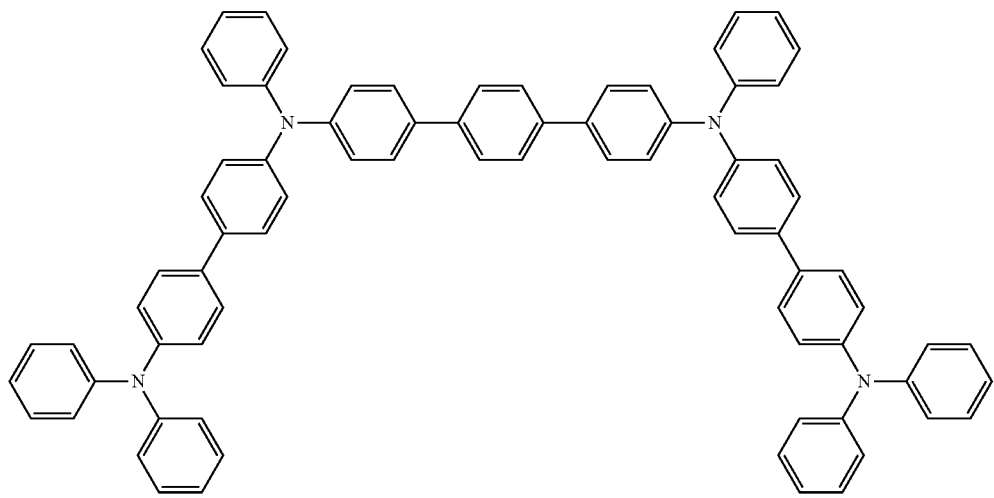
[Chemical Formula 45]
(1-39)
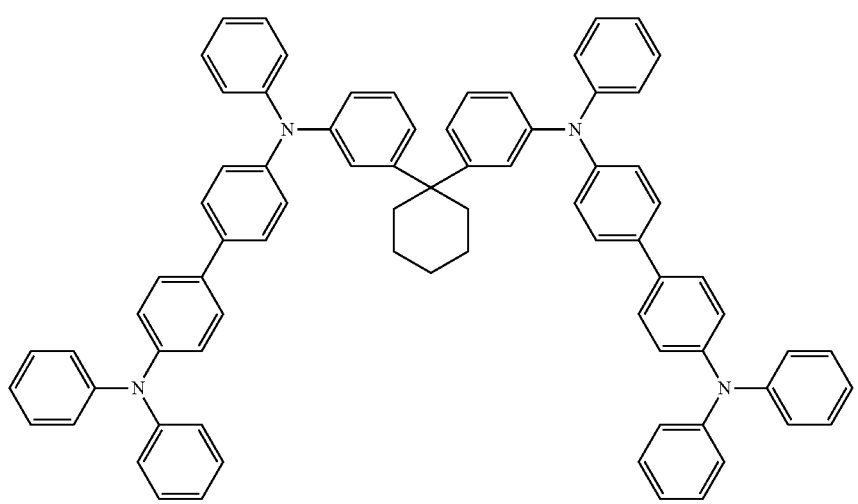
[Chemical Formula 46]
(1-40)
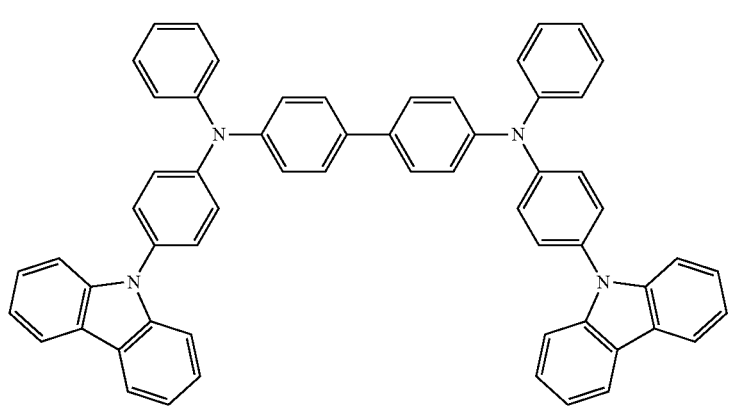

[Chemical Formula 47]
(1-41)
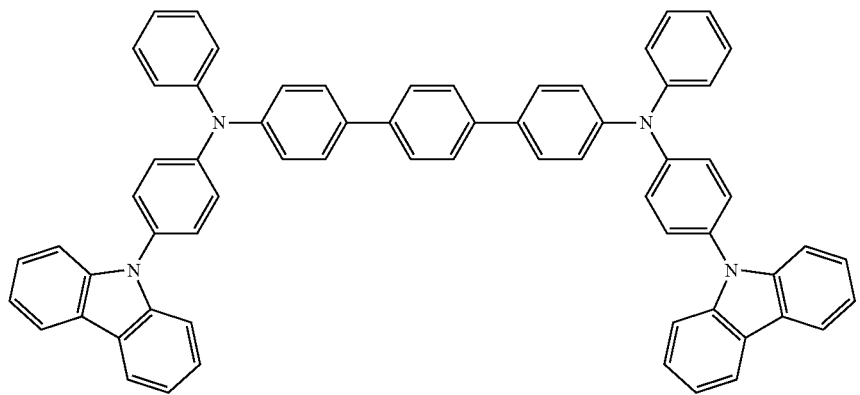
[Chemical Formula 48]
(1-42)
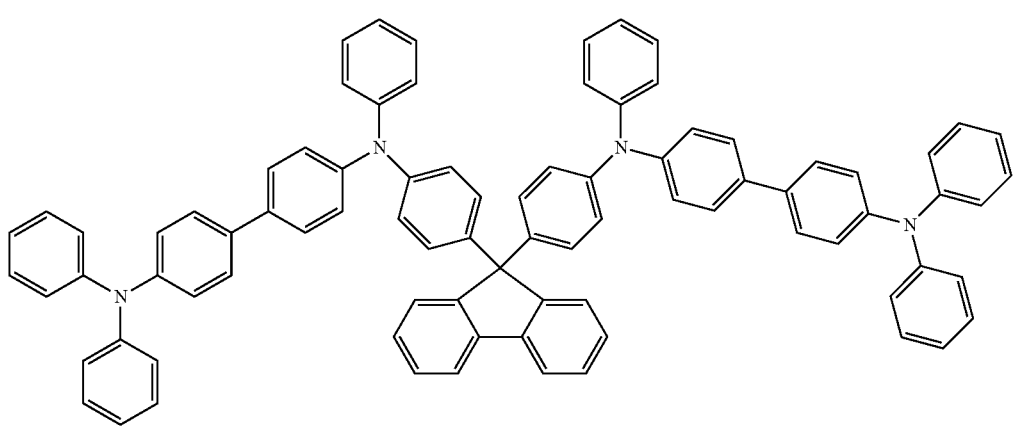
[Chemical Formula 49]
(1-43)
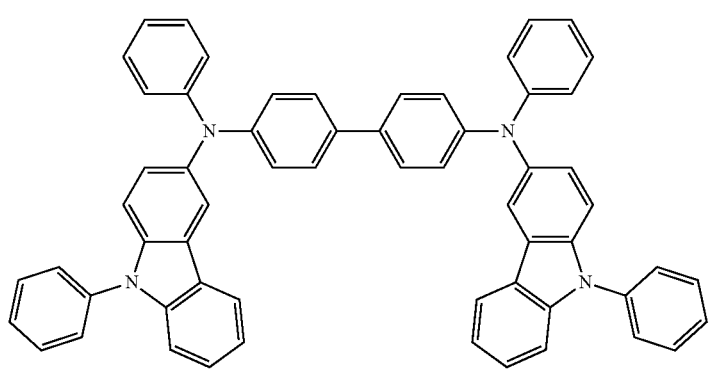

[Chemical Formula 50]
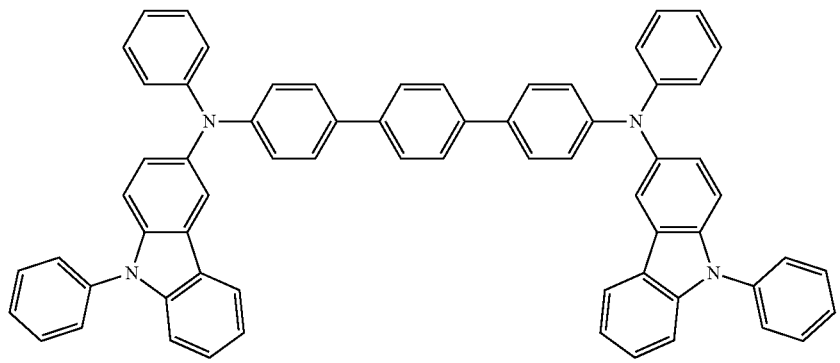
(1-44)
[Chemical Formula 51]
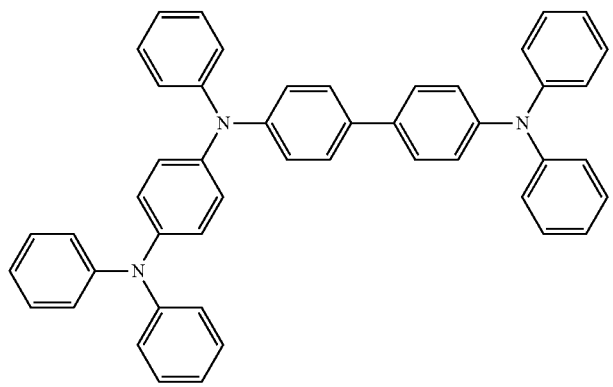
(1-45)
[Chemical Formula 52]
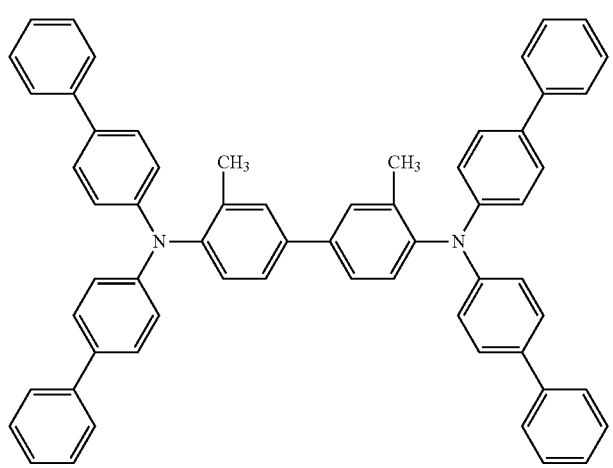
(1-46)

[Chemical Formula 53]

(1-47)

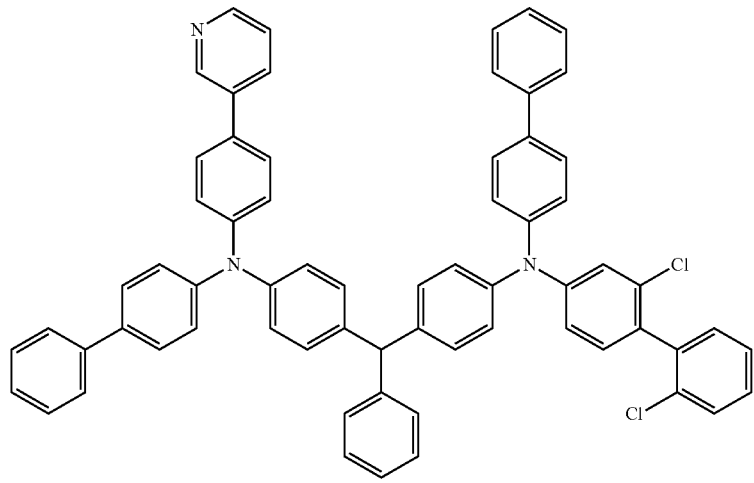

The following presents specific examples of preferred compounds in addition to the arylamine compounds (X') each having a structure in which two triphenylamine structures are joined within a molecule via a single bond or a divalent group that does not contain a heteroatom, represented by the general formula (1) in the arylamine compounds (X) each having a structure in which two triphenylamine structures are joined within a molecule via a single bond or a divalent group that does not contain a heteroatom, suitably used for the organic EL device of the present invention. The present invention, however, is not restricted to these compounds.

[Chemical Formula 54]

(1'-1)

[Chemical Formula 55]

(1'-2)

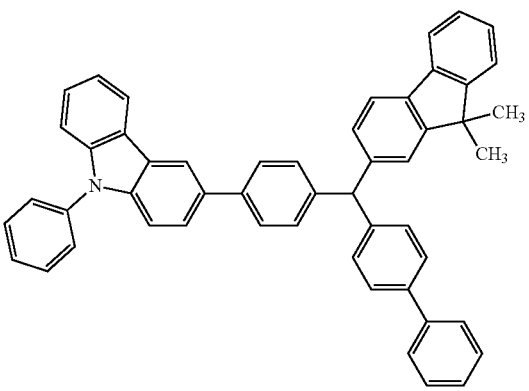

These compounds were purified by methods such as column chromatography, adsorption using silica gel, activated carbon, activated clay, or the like, and recrystallization or crystallization using a solvent, and purified by sublimation or the like in the end. Melting points, glass transition points (Tg), and refractive indexes were measured as physical values. The melting point can be used as an index of vapor deposition property, the glass transition point (Tg) as an index of stability in a thin film state, and the refractive index as an index in regard to the improvement of light extraction efficiency.

The melting points and the glass transition points (Tg) were measured using powder, with a high-sensitive differential scanning calorimeter (DSC3100S made by Bruker AXS).

For the measurement of the refractive indexes, a thin film of 60 nm was fabricated on a silicon substrate, and a compact high-speed spectroscopic ellipsometer (UNECS-2000 made by Ulvac, Inc.) was used.

The organic EL device of the present invention may have a structure including an anode made of metal, a hole transport layer, a light emitting layer, an electron transport layer, a semitransparent cathode, and a capping layer successively formed on a glass substrate in a light emitting device of top emission structure, optionally with a hole injection layer between the anode and the hole transport layer, an electron blocking layer between the hole transport layer and the light emitting layer, a hole blocking layer between the light emitting layer and the electron transport layer, and an electron injection layer between the electron transport layer and the cathode. Some of the organic layers in this multilayer structure may be omitted or combined. For example, the organic EL device may be configured to combine the hole transport layer with the electron blocking layer and to combine the electron transport layer with the hole blocking layer. The total of film thickness of the respective layers of the organic EL device is preferably about 200 nm to 750 nm, further preferably about 350 nm to 600 nm. The film thickness of the capping layer is preferably 30 nm to 120 nm, for example, and further preferably 40 nm to 80 nm. In this case, excellent light extraction efficiency can be obtained. The film thickness of the capping layer may be suitably changed according to the kind of a light emitting material used for the light emitting device, the thickness of the organic EL device excluding the capping layer, and the like.

An electrode material with a large work function such as ITO or gold is used for the anode of the organic EL device of the present invention.

The hole injection layer of the organic EL device of the present invention may be made of materials, the examples of which include an arylamine compound having a structure in which three or more triphenylamine structures are joined within a molecule via a single bond or a divalent group that does not contain a heteroatom, such as starburst-type triphenylamine derivatives and various triphenylamine tetramers; porphyrin compounds represented by copper phthalocyanine; accepting heterocyclic compounds such as hexacyano azatriphenylene; and coating-type polymer materials. These materials may be individually formed into films, or may be used as a single layer formed into a film as a mixture with other materials, or may be formed into a laminated structure of individually formed layers, a laminated structure of mixedly formed layers, or a laminated structure of the individually formed layer and the mixedly formed layer. These materials may be formed into a thin film by a vapor deposition method or other known methods such as a spin coating method and an inkjet method.

Preferred examples of material used for the hole transport layer of the organic EL device of the present invention include N,N'-diphenyl-N,N'-di(m-tolyl)benzidine (hereinafter referred to as TPD), N,N'-diphenyl-N,N'-di(α-naphthyl) benzidine (hereinafter referred to as NPD), 1,1-bis[4-(di-4-tolylamino)phenyl]cyclohexane (hereinafter referred to as TAPC), particularly an arylamine compound having a structure in which two triphenylamine structures are joined within a molecule via a single bond or a divalent group that does not contain a heteroatom, represented by the general formula (1), such as N,N,N',N'-tetrabiphenylylbenzidine, and an arylamine compound having a structure in which three or more triphenylamine structures are joined within a molecule via a single bond or a divalent group that does not contain a heteroatom, such as various triphenylamine trimers and tetramers. These materials may be individually formed into films, or may be used as a single layer formed into a film as a mixture with other materials, or may be formed into a laminated structure of individually formed layers, a laminated structure of mixedly formed layers, or a laminated structure of the individually formed layer and the mixedly formed layer. These materials may be formed into a thin film by a vapor deposition method or other known methods such as a spin coating method and an inkjet method.

Material used for the hole injection layer or the hole transport layer may be obtained by p-doping trisbromophenylamine hexachloroantimony or the like into the material commonly used for these layers, or may be, for example, polymer compounds each having a TPD structure as a part of the compound structure.

Examples of material used for the electron blocking layer of the organic EL device of the present invention can be compounds having an electron blocking effect, including carbazole derivatives such as 4,4',4"-tri(N-carbazolyl)triphenylamine (hereinafter referred to as TCTA), 9,9-bis[4-(carbazol-9-yl)phenyl]fluorene, 1,3-bis(carbazol-9-yl)benzene (hereinafter referred to as mCP), and 2,2-bis(4-carbazol-9-ylphenyl)adamantane (hereinafter referred to as Ad-Cz); and compounds having a triphenylsilyl group and a triarylamine structure, as represented by 9-[4-(carbazol-9-yl)phenyl]-9-[4-(triphenylsilyl)phenyl]-9H-fluorene. These materials may be individually formed into films, or may be used as a single layer formed into a film as a mixture with other materials, or may be formed into a laminated structure of individually formed layers, a laminated structure of mixedly formed layers, or a laminated structure of the individually formed layer and the mixedly formed layer. These materials may be formed into a thin film by a vapor deposition method or other known methods such as a spin coating method and an inkjet method.

Examples of material used for the light emitting layer of the organic EL device of the present invention can be quinolinol derivative metal complexes such as $Alq_3$, various metal complexes, anthracene derivatives, bis(styryl)benzene derivatives, pyrene derivatives, oxazole derivatives, and polyparaphenylene vinylene derivatives. The light emitting layer may include a host material and a dopant material. Examples of the host material can be thiazole derivatives, benzimidazole derivatives, and polydialkyl fluorene derivatives, in addition to the above light-emitting materials. Examples of the dopant material can be quinacridone, coumarin, rubrene, perylene, derivatives thereof, benzopyran derivatives, rhodamine derivatives, and aminostyryl derivatives. These materials may be individually formed into films, or may be used as a single layer formed into a film as a mixture with other materials, or may be formed into a laminated structure of individually formed layers, a laminated structure of mixedly formed layers, or a laminated structure of the individually formed layer and the mixedly formed layer.

The light-emitting material may be a phosphorescent light-emitting material. Phosphorescent materials as metal complexes of metals such as iridium and platinum may be used as the phosphorescent light-emitting material. Examples of the phosphorescent materials can be green phosphorescent materials such as $Ir(ppy)_3$, blue phosphorescent materials such as FIrpic and FIr6, and red phosphorescent materials such as $Btp_2Ir(acac)$. As the host materials, examples of hole injecting and transporting host materials can be carbazole derivatives such as 4,4'-di(N-carbazolyl) biphenyl (hereinafter referred to as CBP), TCTA, and mCP, and examples of electron transporting host materials can be p-bis(triphenylsilyl)benzene (hereinafter referred to as UGH2) and 2,2',2"-(1,3,5-phenylene)-tris(1-phenyl-1H- benzimidazole) (hereinafter referred to as TPBI) to produce a high-performance organic EL device.

In order to avoid concentration quenching, it is preferable to dope the host material with the phosphorescent light-emitting material by co-evaporation in a range of 1 to 30 weight percent to the whole light emitting layer.

These materials may be formed into a thin film by using a vapor deposition method or other known methods such as a spin coating method and an inkjet method.

The hole blocking layer of the organic EL device of the present invention may be formed by using hole blocking compounds such as metal complexes of phenanthroline derivatives, e.g. bathocuproin (hereinafter referred to as BCP), metal complexes of quinolinol derivatives, e.g. aluminum(III) bis(2-methyl-8-quinolinate)-4-phenylphenolate (hereinafter referred to as BAlq), various rare earth complexes, triazole derivatives, triazine derivatives, and oxadiazole derivatives. These materials may also serve as the material of the electron transport layer. These materials may be individually formed into films, or may be used as a single layer formed into a film as a mixture with other materials, or may be formed into a laminated structure of individually formed layers, a laminated structure of mixedly formed layers, or a laminated structure of the individually formed layer and the mixedly formed layer. These materials may be formed into a thin film by a vapor deposition method or other known methods such as a spin coating method and an inkjet method.

The electron transport layer of the organic EL device of the present invention may be formed by using metal complexes of quinolinol derivatives such as $Alq_3$ and BAlq, various metal complexes, triazole derivatives, triazine derivatives, oxadiazole derivatives, thiadiazole derivatives, pyridoindole derivatives, carbodiimide derivatives, quinoxaline derivatives, phenanthroline derivatives, and silole derivatives. These materials may be individually formed into films, or may be used as a single layer formed into a film as a mixture with other materials, or may be formed into a laminated structure of individually formed layers, a laminated structure of mixedly formed layers, or a laminated structure of the individually formed layer and the mixedly formed layer. These materials may be formed into a thin film by a vapor deposition method or other known methods such as a spin coating method and an inkjet method.

The electron injection layer of the organic EL device of the present invention may be formed by using alkali metal salts such as lithium fluoride and cesium fluoride; alkaline earth metal salts such as magnesium fluoride; and metal oxides such as aluminum oxide. However, the electron injection layer may be omitted in the preferred selection of the electron transport layer and the cathode.

The electron injection layer or the electron transport layer may be one obtained by the N-doping of metals such as cesium in the materials commonly used for these layers.

The semitransparent cathode of the organic EL device of the present invention may be made of an electrode material having a low work function such as aluminum; an alloy having an even lower work function such as a magnesium-silver alloy, a magnesium-calcium alloy, a magnesium-indium alloy, or an aluminum-magnesium alloy; or ITO or IZO as an electrode material.

The capping layer of the organic EL device of the present invention is preferably made of an arylamine compound having a structure in which two triphenylamine structures are joined within a molecule via a single bond or a divalent group that does not contain a heteroatom, represented by the general formula (1), such as N,N,N',N'-tetrabiphenylylbenzidine. These materials may be individually formed into films, or may be used as a single layer formed into a film as a mixture with other materials, or may be formed into a laminated structure of individually formed layers, a laminated structure of mixedly formed layers, or a laminated structure of the individually formed layer and the mixedly formed layer. These materials may be formed into a thin film by a vapor deposition method or other known methods such as a spin coating method and an inkjet method.

The FIGURE shows the organic EL device of top emission structure. The present invention, however, is not restricted to the organic EL device of top emission structure but is also applicable to an organic EL device of bottom emission structure and an organic EL device of dual emission structure that emits light from both top and bottom directions. In these cases, an electrode present in a direction to extract light from a light emitting device to the exterior is required to be transparent or semitransparent.

It is preferable that the refractive index of the material that composes the capping layer is larger than that of an adjacent electrode. That is, light extraction efficiency in the organic EL device is improved by the capping layer. Its effect, however, is valid because the effect of light interference is larger when the reflectance at an interface between the capping layer and material in contact with the capping layer is larger. Consequently, the refractive index of the material that composes the capping layer is preferably larger than that of the adjacent electrode, and the refractive index is required to be 1.70 or more, further preferably 1.75 or more, and particularly preferably 1.80 or more.

The following describes an embodiment of the present invention in more detail based on Examples. The present invention, however, is not restricted to the following Examples.

Example 1

The melting points and the glass transition points of the compounds of the present invention were determined using a high-sensitive differential scanning calorimeter (DSC 3100S made by Bruker AXS).

|  | Melting point | Glass transition point |
|---|---|---|
| Exemplified Compound (1-1) | 265° C. | 132° C. |
| Exemplified Compound (1-13) | 216° C. | 103° C. |
| Exemplified Compound (1-14) | 218° C. | 160° C. |
| Exemplified Compound (1-17) | 273° C. | 108° C. |
| Exemplified Compound (1-18) | 266° C. | 106° C. |
| Exemplified Compound (1-27) | 258° C. | 126° C. |
| Exemplified Compound (1-32) | 153° C. | 107° C. |
| Exemplified Compound (1-33) | 210° C. | 113° C. |
| Exemplified Compound (1-36) | 160° C. | 125° C. |
| Exemplified Compound (1-37) | 168° C. | 144° C. |
| Exemplified Compound (1-46) | 251° C. | 128° C. |

The compounds of the present invention have the glass transition points of 100° C. or higher. This indicates that the compounds of the present invention have a stable thin-film state.

Example 2

A vapor-deposited film with a film thickness of 60 nm was fabricated on a silicon substrate using the compounds of the present invention, and the refractive indexes of 633 nm were measured using the compact high-speed spectroscopic ellipsometer (UNECS-2000 made by Ulvac, Inc.).

| | Refractive Index |
|---|---|
| Exemplified Compound (1-1) | 1.81 |
| Exemplified Compound (1-13) | 1.78 |
| Exemplified Compound (1-14) | 1.76 |
| Exemplified Compound (1-17) | 1.79 |
| Exemplified Compound (1-18) | 1.88 |
| Exemplified Compound (1-27) | 1.82 |
| Exemplified Compound (1-32) | 1.80 |
| Exemplified Compound (1-33) | 1.89 |
| Exemplified Compound (1-36) | 1.76 |
| Exemplified Compound (1-37) | 1.85 |
| Exemplified Compound (1-42) | 1.76 |
| Exemplified Compound (1-46) | 1.78 |
| Comparative Compound (Alq$_3$) | 1.70 |

The compounds of the present invention thus have values larger than the refractive index 1.70 of Comparative Compound (Alq$_3$), and large improvement of light extraction efficiency in an organic EL device can be expected.

Example 3

The organic EL device was fabricated by vapor-depositing a hole injection layer 3, a hole transport layer 4, a light emitting layer 5, an electron transport layer 6, an electron injection layer 7, a cathode 8 and a capping layer 9 in this order on a glass substrate 1 on which a reflecting ITO electrode was formed as a metal anode 2 beforehand as shown in the FIGURE.

Specifically, the glass substrate 1 having ITO (thickness 150 nm) formed thereon was subjected to ultrasonic washing in isopropyl alcohol for 20 minutes and then dried for 10 minutes on a hot plate heated to 250° C. After UV ozone treatment for 2 minutes, the glass substrate with ITO was installed in a vacuum vapor deposition apparatus, and the pressure was reduced to 0.001 Pa or lower. This was followed by formation of the hole injection layer 3 by forming Compound 2 of the structural formula below to cover the metal anode 2 in a film thickness of 60 nm at a vapor deposition rate of 6 nm/min. The hole transport layer 4 was then formed on the hole injection layer 3 by forming Exemplified Compound (1-13) of the structural formula above in a film thickness of 40 nm at a vapor deposition rate of 6 nm/min. The light emitting layer 5 was formed on the hole transport layer 4 in a film thickness of 30 nm by dual vapor deposition of Compound 3 of the structural formula below and Compound 4 of the structural formula below at a vapor deposition rate ratio of Compound 3:Compound 4=5:95. The electron transport layer 6 was formed on the light emitting layer 5 by forming Compound 5 of the structural formula below in a film thickness of 30 nm at a vapor deposition rate of 6 nm/min. The electron injection layer 7 was formed on the electron transport layer 6 by forming lithium fluoride in a film thickness of 0.5 nm at a vapor deposition rate of 0.6 nm/min. The cathode 8 was formed on the electron injection layer 7 by forming a magnesium silver alloy in a film thickness of 10 nm. Finally, Exemplified Compound (1-13) was formed as the capping layer 9 in a film thickness of 60 nm at a vapor deposition rate of 6 nm/min.

The characteristics of the thus fabricated organic EL device were measured in the atmosphere at an ordinary temperature.

Table 1 summarizes the results of emission characteristics measurements performed by applying DC voltage to the fabricated organic EL device.

[Chemical Formula 56]

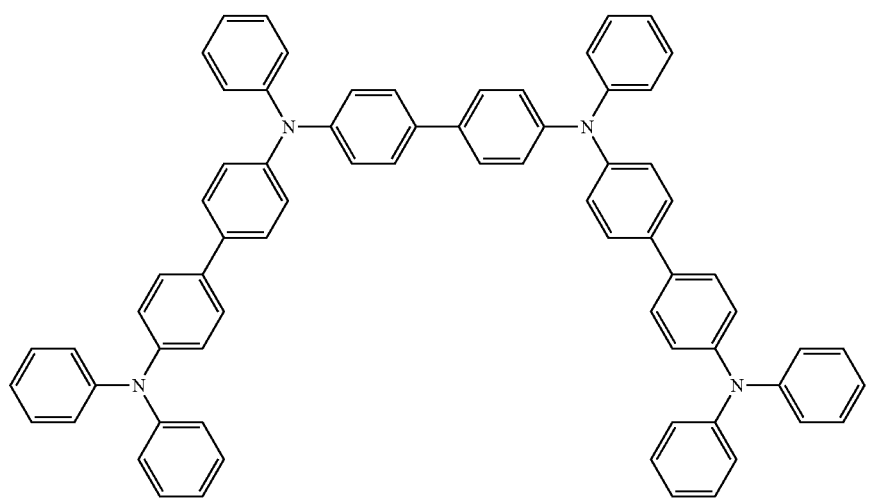

(Compound 2)

[Chemical Formula 57]

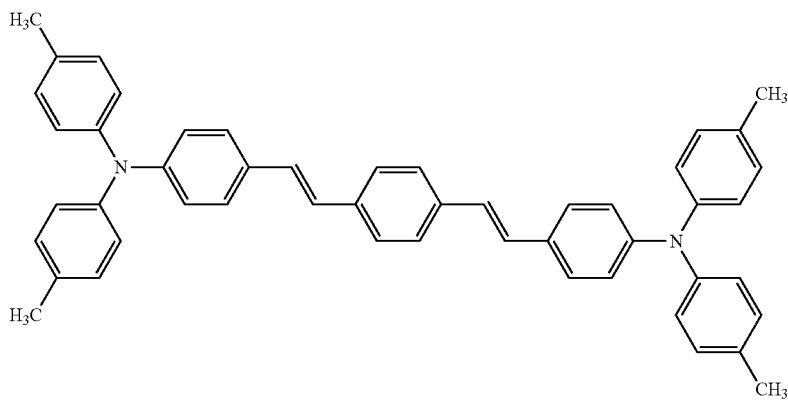

(Compound 3)

[Chemical Formula 58]

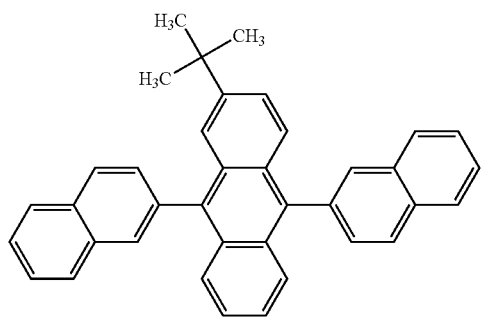

(Compound 4)

[Chemical Formula 59]

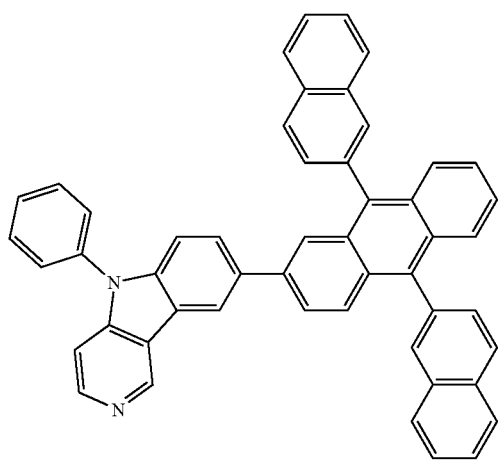

(Compound 5)

Example 4

An organic EL device was fabricated under the same conditions used in Example 3, except that the capping layer 9 was formed by forming Exemplified Compound (1-17) in a thickness of 60 nm, instead of using Exemplified Compound (1-13). The characteristics of the fabricated organic EL device were measured in the atmosphere at an ordinary temperature. Table 1 summarizes the results of the emission characteristics measurements performed by applying DC voltage to the fabricated organic EL device.

Example 5

An organic EL device was fabricated under the same conditions used in Example 3, except that the capping layer 9 was formed by forming Exemplified Compound (1-18) in a thickness of 60 nm, instead of using Exemplified Compound (1-13). The characteristics of the fabricated organic EL device were measured in the atmosphere at an ordinary temperature. Table 1 summarizes the results of the emission characteristics measurements performed by applying DC voltage to the fabricated organic EL device.

Example 6

An organic EL device was fabricated under the same conditions used in Example 3, except that the capping layer 9 was formed by forming Exemplified Compound (1-27) in a thickness of 60 nm, instead of using Exemplified Compound (1-13). The characteristics of the fabricated organic EL device were measured in the atmosphere at an ordinary temperature. Table 1 summarizes the results of the emission characteristics measurements performed by applying DC voltage to the fabricated organic EL device.

Example 7

An organic EL device was fabricated under the same conditions used in Example 3, except that the capping layer 9 was formed by forming Exemplified Compound (1-32) in a thickness of 60 nm, instead of using Exemplified Compound (1-13). The characteristics of the fabricated organic EL device were measured in the atmosphere at an ordinary temperature. Table 1 summarizes the results of the emission characteristics measurements performed by applying DC voltage to the fabricated organic EL device.

Example 8

An organic EL device was fabricated under the same conditions used in Example 3, except that the capping layer 9 was formed by forming Exemplified Compound (1-33) in a thickness of 60 nm, instead of using Exemplified Compound (1-13). The characteristics of the fabricated organic EL device were measured in the atmosphere at an ordinary temperature. Table 1 summarizes the results of the emission characteristics measurements performed by applying DC voltage to the fabricated organic EL device.

Example 9

An organic EL device was fabricated under the same conditions used in Example 3, except that the capping layer 9 was formed by forming Exemplified Compound (1-36) in a thickness of 60 nm, instead of using Exemplified Compound (1-13). The characteristics of the fabricated organic EL device were measured in the atmosphere at an ordinary temperature. Table 1 summarizes the results of the emission characteristics measurements performed by applying DC voltage to the fabricated organic EL device.

Example 10

An organic EL device was fabricated under the same conditions used in Example 3, except that the capping layer 9 was formed by forming Exemplified Compound (1-37) in a thickness of 60 nm, instead of using Exemplified Compound (1-13). The characteristics of the fabricated organic EL device were measured in the atmosphere at an ordinary temperature. Table 1 summarizes the results of the emission characteristics measurements performed by applying DC voltage to the fabricated organic EL device.

Comparative Example 1

An organic EL device was fabricated under the same conditions used in Example 3, except that the capping layer 9 was formed by forming $Alq_3$ in a thickness of 60 nm, instead of using Exemplified Compound (1-13). The characteristics of the fabricated organic EL device were measured in the atmosphere at an ordinary temperature. Table 1 summarizes the results of the emission characteristics measurements performed by applying DC voltage to the fabricated organic EL device.

TABLE 1

| | | Voltage [V] (@ 10 mA/cm$^2$) | Luminance [cd/m$^2$] (@ 10 mA/cm$^2$) | Current efficiency [cd/A] (@ 10 mA/cm$^2$) | Power efficiency [lm/W] (@ 10 mA/cm$^2$) | External quantum efficiency [%] (@ 10 mA/cm$^2$) |
|---|---|---|---|---|---|---|
| Ex. 3 | Exemplified Compound (1-13) | 4.17 | 538 | 5.38 | 4.05 | 10.94 |
| Ex. 4 | Exemplified Compound (1-17) | 4.11 | 504 | 5.04 | 3.85 | 10.45 |
| Ex. 5 | Exemplified Compound (1-18) | 4.13 | 526 | 5.26 | 4.00 | 10.82 |
| Ex. 6 | Exemplified Compound (1-27) | 4.18 | 507 | 5.07 | 3.81 | 10.35 |
| Ex. 7 | Exemplified Compound (1-32) | 4.12 | 541 | 5.41 | 4.12 | 11.10 |
| Ex. 8 | Exemplified Compound (1-33) | 4.16 | 531 | 5.31 | 4.00 | 10.81 |
| Ex. 9 | Exemplified Compound (1-36) | 4.14 | 506 | 5.06 | 3.83 | 10.40 |
| Ex. 10 | Exemplified Compound (1-37) | 4.11 | 528 | 5.28 | 4.03 | 10.89 |
| Com. Ex. 1 | Alq$_3$ | 4.15 | 496 | 4.96 | 3.75 | 10.20 |

As shown in Table 1, the driving voltage at a current density of 10 mA/cm$^2$ in Examples 3 to 10 was substantially equivalent to that in Comparative Example 1 using Alq$_3$, while luminance, current efficiency and power efficiency were all improved. Further, a great improvement in external quantum efficiency could be confirmed. This indicates that light extraction efficiency can be greatly improved by containing, in the capping layer, a material having a high refractive index and suitably used for the organic EL device of the present invention.

INDUSTRIAL APPLICABILITY

As demonstrated above, the arylamine compound having a structure in which two triphenylamine structures are joined within a molecule via a single bond or a divalent group that does not contain a heteroatom, suitably used for the organic EL device of the present invention, excels as the compound for the organic EL device because of having a high refractive index, attaining a great improvement in light extraction efficiency and having a stable thin-film state. High efficiency can be obtained, and durability can be improved by fabricating the organic EL device using this compound. The use of this compound having no absorption in the respective wavelength ranges of blue, green, and red is particularly suitable in the case of displaying a clear, light image with high color purity. For example, development to application of domestic electrical appliances and illumination can be achieved.

DESCRIPTION OF REFERENCE NUMERAL

1 Glass substrate
2 Metal anode
3 Hole injection layer
4 Hole transport layer
5 Light emitting layer
6 Electron transport layer
7 Electron injection layer
8 Cathode
9 Capping layer

What is claimed is:

1. An organic electroluminescent device comprising at least an anode electrode, a hole transport layer, a light emitting layer, an electron transport layer, a cathode electrode, and a capping layer in this order, wherein the capping layer is the outermost layer of the organic electroluminescent device and the capping layer comprises an arylamine compound (X') represented by the following general formula (1):

[Chemical Formula 1]

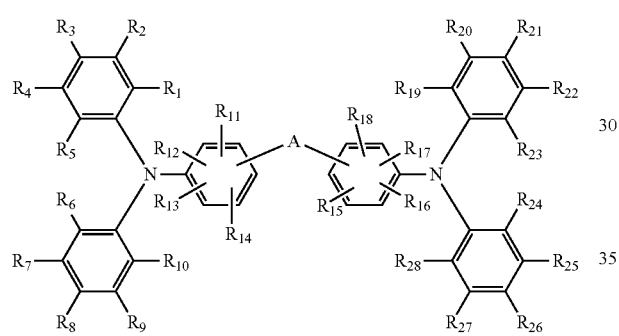

(1)

wherein $R_1$ to $R_{28}$ may be the same or different, and each represents a hydrogen atom, a deuterium atom, a fluorine atom, a chlorine atom, cyano, trifluoromethyl, nitro, linear or branched alkyl of 1 to 6 carbon atoms that may have a substituent, linear or branched alkenyl of 2 to 6 carbon atoms that may have a substituent, cycloalkyl of 5 to 10 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, where these substituents may bind to each other to form a ring when a plurality of these substituents bind to the same benzene ring; $R_1$ to $R_{10}$ and $R_{19}$ to $R_{28}$ may form rings by binding to benzene rings to which the respective groups bind; and A represents a divalent group represented by the following structural formula (B) or a single bond, where at least one of $R_1$ to $R_{28}$ is a substituted or unsubstituted aromatic heterocyclic group selected from pyridyl, pyranyl, indolyl, benzooxazolyl, benzothiazolyl, pyrazolyl, and carbolinyl, and at least one of $R_1$ to $R_5$, $R_6$ to $R_{10}$, $R_{19}$ to $R_{23}$, or $R_{24}$ to $R_{28}$ is a deuterium atom, a fluorine atom, a chlorine atom, cyano, trifluoromethyl, nitro, linear or branched alkyl of 1 to 6 carbon atoms that may have a substituent, linear or branched alkenyl of 2 to 6 carbon atoms that may have a substituent, cycloalkyl of 5 to 10 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic heterocyclic group, a substituted or unsubstituted condensed polycyclic aromatic group, or substituted or unsubstituted aryloxy, where these substituents may bind to each other to form a ring when a plurality of these substituents bind to the same benzene ring,

[Chemical Formula 2]

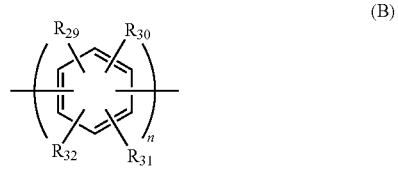

(B)

wherein $R_{29}$ to $R_{32}$ may be the same or different, and each represents a hydrogen atom, a deuterium atom, a fluorine atom, a chlorine atom, cyano, trifluoromethyl, linear or branched alkyl of 1 to 6 carbon atoms, linear or branched alkenyl of 2 to 6 carbon atoms, a substituted or unsubstituted aromatic hydrocarbon group, a substituted or unsubstituted aromatic heterocyclic group, or a substituted or unsubstituted condensed polycyclic aromatic group, where these substituents may bind to each other to form a ring when a plurality of these substituents bind to the same benzene ring; and n is an integer of 1 to 3, where when a plurality of each of $R_{29}$ to $R_{32}$ are present (when n is 2 or 3), $R_{29}$ to $R_{32}$ may be the same or different.

2. The organic electroluminescent device according to claim 1, wherein A is a divalent group represented by the structural formula (B), and n is 1 in the general formula (1).

3. The organic electroluminescent device according to claim 1, wherein A is a single bond in the general formula (1).

4. The organic electroluminescent device according to claim 1, wherein at least one of R1 to R5 is a substituted or unsubstituted aromatic heterocyclic group selected from pyridyl, furanyl, pyranyl, thienyl, quinolyl, isoquinolyl, benzofuranyl, indolyl, carbazolyl, benzooxazolyl, benzothiazolyl, quinoxalyl, benzoimidazolyl, pyrazolyl, dibenzofuranyl, dibenzothienyl, and carbolinyl.

5. The organic electroluminescent device according to claim 1, wherein at least one of R1 to R5 is a substituted or unsubstituted aromatic heterocyclic group selected from pyridyl, furanyl, pyranyl, thienyl, quinolyl, isoquinolyl, benzofuranyl, indolyl, carbazolyl, benzooxazolyl, benzothiazolyl, quinoxalyl, benzoimidazolyl, pyrazolyl, dibenzofuranyl, dibenzothienyl, and carboliny, and at least one of R6 to R10 is a substituted or unsubstituted aromatic heterocyclic group selected from pyridyl, furanyl, pyranyl, thienyl, quinolyl, isoquinolyl, benzofuranyl, indolyl, carbazolyl, benzooxazolyl, benzothiazolyl, quinoxalyl, benzoimidazolyl, pyrazolyl, dibenzofuranyl, dibenzothienyl, and carbolinyl.

6. The organic electroluminescent device according to claim 1, wherein at least one of R1 to R5 is a substituted or unsubstituted aromatic heterocyclic group selected from pyridyl, furanyl, pyranyl, thienyl, quinolyl, isoquinolyl, benzofuranyl, indolyl, carbazolyl, benzooxazolyl, benzothiazolyl, quinoxalyl, benzoimidazolyl, pyrazolyl, dibenzofuranyl, dibenzothienyl, and carbolinyl, and at least one of R19 to R23 is a substituted or unsubstituted aromatic heterocyclic group selected from pyridyl, furanyl, pyranyl, thienyl, quinolyl, isoquinolyl, benzofuranyl, indolyl, carbazolyl, benzooxazolyl, benzothiazolyl, quinoxalyl, benzoimidazolyl, pyrazolyl, dibenzofuranyl, dibenzothienyl, and carbolinyl.

7. The organic electroluminescent device according to claim 1, wherein the thickness of the capping layer is within a range of 30 nm to 120 nm.

8. The organic electroluminescent device according to claim 2, wherein the thickness of the capping layer is within a range of 30 nm to 120 nm.

9. The organic electroluminescent device according to claim 3, wherein the thickness of the capping layer is within a range of 30 nm to 120 nm.

10. The organic electroluminescent device according to claim 4, wherein the thickness of the capping layer is within a range of 30 nm to 120 nm.

11. The organic electroluminescent device according to claim 5, wherein the thickness of the capping layer is within a range of 30 nm to 120 nm.

12. The organic electroluminescent device according to claim 1, wherein the refractive index of the capping layer is 1.75 or more when the wavelength of light that transmits the capping layer is within a range of 530 nm to 750 nm.

13. The organic electroluminescent device according to claim 2, wherein the refractive index of the capping layer is 1.75 or more when the wavelength of light that transmits the capping layer is within a range of 530 nm to 750 nm.

14. The organic electroluminescent device according to claim 3, wherein the refractive index of the capping layer is 1.75 or more when the wavelength of light that transmits the capping layer is within a range of 530 nm to 750 nm.

15. The organic electroluminescent device according to claim 4, wherein the refractive index of the capping layer is 1.75 or more when the wavelength of light that transmits the capping layer is within a range of 530 nm to 750 nm.

16. The organic electroluminescent device according to claim 7, wherein the refractive index of the capping layer is 1.75 or more when the wavelength of light that transmits the capping layer is within a range of 530 nm to 750 nm.

17. A method for using a compound represented by the following general formula (1) for an outermost capping layer of an organic electroluminescent device

[Chemical Formula 3]

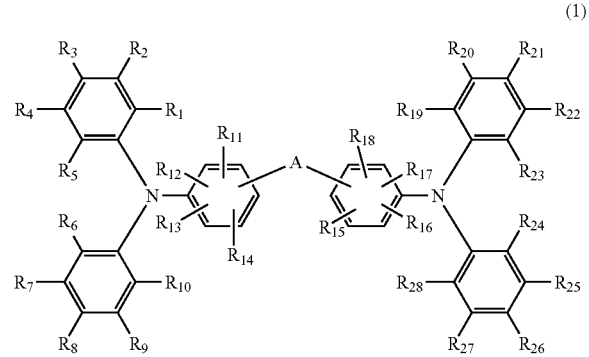

(1)

wherein $R_1$ to $R_{28}$ may be the same or different, and each represents a hydrogen atom, a deuterium atom, a fluorine atom, a chlorine atom, cyano, trifluoromethyl, nitro, linear or branched alkyl of 1 to 6 carbon atoms that may have a substituent, linear or branched alkenyl of 2 to 6 carbon atoms that may have a substituent, cycloalkyl of 5 to 10 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, where these substituents may bind to each other to form a ring when a plurality of these substituents bind to the same benzene ring; $R_1$ to $R_{10}$ and $R_{19}$ to $R_{28}$ may form rings by binding to benzene rings to which the respective groups bind; and A represents a divalent group represented by the following structural formula (B) or a single bond, where at least one of $R_1$ to $R_{28}$ is a substituted or unsubstituted aromatic heterocyclic group selected from pyridyl, pyranyl, indolyl, benzooxazolyl, benzothiazolyl, pyrazolyl, and carbolinyl, and wherein at least one of $R_1$ to $R_5$, $R_6$ to $R_{10}$, $R_{19}$ to $R_{23}$, or $R_{24}$ to $R_{28}$ is a deuterium atom, a fluorine atom, a chlorine atom, cyano, trifluoromethyl, nitro, linear or branched alkyl of 1 to 6 carbon atoms that may have a substituent, linear or branched alkenyl of 2 to 6 carbon atoms that may have a substituent, cycloalkyl of 5 to 10 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic heterocyclic group, a substituted or unsubstituted condensed polycyclic aromatic group, or substituted or unsubstituted aryloxy, where these substituents may bind to each other to form a ring when a plurality of these substituents bind to the same benzene ring;

[Chemical Formula 4]

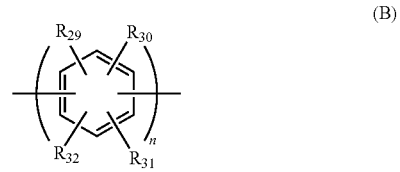

(B)

wherein $R_{29}$ to $R_{32}$ may be the same or different, and each represents a hydrogen atom, a deuterium atom, a fluorine atom, a chlorine atom, cyano, trifluoromethyl, linear or branched alkyl of 1 to 6 carbon atoms, linear or branched alkenyl of 2 to 6 carbon atoms, a substituted or unsubstituted aromatic hydrocarbon group, a substituted or unsubstituted aromatic heterocyclic group, or a substituted or unsubstituted condensed polycyclic aromatic group, where these substituents may bind to each other to form a ring when a plurality of these substituents bind to the same benzene ring; and n is an integer of 1 to 3, where when a plurality of each of $R_{29}$ to $R_{32}$ are present (when n is 2 or 3), $R_{29}$ to $R_{32}$ may be the same or different.

* * * * *